United States Patent
Bruder et al.

(10) Patent No.: US 9,831,042 B2
(45) Date of Patent: Nov. 28, 2017

(54) ORGANIC DYES COMPRISING A HYDRAZONE MOIETY AND THEIR USE IN DYE-SENSITIZED SOLAR CELLS

(71) Applicant: BASF SE, Ludwigshafen (DE)

(72) Inventors: Ingmar Bruder, Mutterstadt (DE); Robert Send, Karlsruhe (DE); Simona Urnikaite, Kaunas (LT); Tadas Malinauskas, Kaunas (LT); Maryte Daskeviciene, Jonava (LT); Vytautas Getautis, Kaunas (LT)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/992,761

(22) Filed: Jan. 11, 2016

(65) Prior Publication Data

US 2016/0126022 A1    May 5, 2016

Related U.S. Application Data

(66) Continuation of application No. 13/932,403, filed on Jul. 1, 2013, now abandoned, Substitute for application No. 61/667,971, filed on Jul. 4, 2012.

(51) Int. Cl.
| | |
|---|---|
| C07D 277/36 | (2006.01) |
| H01G 9/20 | (2006.01) |
| H01L 51/00 | (2006.01) |
| C09B 26/02 | (2006.01) |
| C07D 417/12 | (2006.01) |

(52) U.S. Cl.
CPC ......... *H01G 9/2059* (2013.01); *C07D 277/36* (2013.01); *C07D 417/12* (2013.01); *C09B 26/02* (2013.01); *H01L 51/0059* (2013.01); *H01G 9/2031* (2013.01); *Y02E 10/542* (2013.01); *Y02E 10/549* (2013.01)

(58) Field of Classification Search
CPC .. C07D 277/36; C07D 417/12; H01G 9/2059; H01G 9/2031; H01L 51/0059; C09B 26/02; Y02E 10/542; Y02E 10/549
See application file for complete search history.

(56) References Cited

U.S. PATENT DOCUMENTS

| | | | |
|---|---|---|---|
| 4,927,721 A | | 5/1990 | Gratzel et al. |
| 4,963,196 A | * | 10/1990 | Hashimoto ....... H01L 31/02167 136/257 |
| 5,350,644 A | | 9/1994 | Graetzel et al. |
| 6,359,211 B1 | | 3/2002 | Spitler et al. |
| 7,118,839 B2 | | 10/2006 | Law et al. |
| 7,202,004 B2 | | 4/2007 | Law et al. |
| 7,358,014 B2 | | 4/2008 | Law et al. |

FOREIGN PATENT DOCUMENTS

| | | | |
|---|---|---|---|
| EP | 0 176 646 A1 | | 4/1986 |
| EP | 1 283 448 A2 | | 2/2003 |
| EP | 1 298 496 A2 | | 4/2003 |
| JP | 06097478 | * | 9/1992 |
| JP | 6-120543 A | | 4/1994 |
| JP | 06097479 | * | 4/1994 |
| JP | 06120543 | * | 4/1994 |
| JP | 10-189065 | | 7/1998 |
| JP | 10-334954 | | 12/1998 |
| JP | 2000-100484 | | 4/2000 |
| JP | 2000-243463 | | 9/2000 |
| JP | 2001-93589 | | 4/2001 |
| JP | 201196436 | * | 12/2001 |

(Continued)

OTHER PUBLICATIONS

Al-Sehemi, J Mol Structure, 2012, 1019, pp. 130-134.*
Al-Sehemi, Spectrochimica Acta Part A: Molecular and Biomolecular Spectroscopy, 2012, vol. 91, 239-243.*
Suresh, Solar Energy Materials & Solar Cells, 2008, vol. 92, 900-908.*
Juozapavicius, Organic Electronics vol. 13, 2012, 23-30.*
CA 121:87572, Mizuta, abstract only of JP 06097476, Apr. 1994.*
International Search Report dated Jan. 2, 2014 in PCT/IB2013/055252.

(Continued)

*Primary Examiner* — D M Seaman

(74) *Attorney, Agent, or Firm* — Oblon, McClelland, Maier & Neustadt, L.L.P.

(57) ABSTRACT

The present invention relates to compounds of general formula I

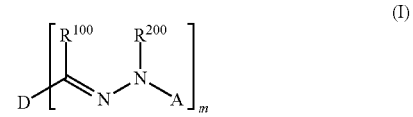

wherein $R^{100}$ and $R^{200}$ are each independently hydrogen, $C_1$-$C_{10}$-alkyl which in case of $C_2$-alkyl may be interrupted by one and in case of $C_3$-$C_{10}$-alkyl by one or two nonadjacent oxygen atoms, $C_5$-$C_7$-cycloalkyl, aryl, aryl-$C_1$-$C_{10}$-alkyl or aryloxy-$C_1$-$C_{10}$-alkyl, D is an m-valent (m=1, 2 or 3) donor moiety which comprises at least one carbon-carbon or carbon-heteroatom double bond and/or at least one unfused or fused carbo- or heterocyclic ring, A is an acceptor moiety which comprises at least one carbon-carbon or carbon-heteroatom double bond and/or at least one unfused or fused carbo- or heterocyclic ring, and the donor moiety D and the acceptor moiety A are π-conjugated to one another.

Furthermore, the present invention relates to the use of compounds of formula I for producing dye-sensitized solar cells and to dye-sensitized solar cells comprising compounds of formula I.

12 Claims, No Drawings

(56) References Cited

FOREIGN PATENT DOCUMENTS

| | | | |
|---|---|---|---|
| JP | 2004146421 | * | 5/2004 |
| JP | 2007013115 | * | 1/2007 |
| WO | WO 2008/132103 A1 | | 11/2008 |
| WO | WO 2012/001628 A1 | | 1/2012 |

OTHER PUBLICATIONS

Lester P. Kuhn et al., "Triphenylmethane Dyes Containing the Hydrazine Group and their Condensation Products with Aldehydes", J. Am. Chem. Soc., vol. 71, Sep. 1949, pp. 3084-3088.

Simona Urnikaite et al., "Simple and Inexpensive Organic Dyes with Hydrazone Moiety as π-Conjugation Bridge for Solid-State Dye-Sensitized Solar Cells", Chemistry—An Asian Journal, vol. 8, No. 3, Jan. 7, 2013, pp. 538-541.

Al-Sehemi et al Spectrochimica Acta Part A: Molecular and Biomolecular Spectroscopy 2012, 91, 239-243—published on-line Jan. 20, 2012.

Suresh et al Solar Energy Materials & Solar Cells 2008, 92, 900-908.

* cited by examiner

ORGANIC DYES COMPRISING A HYDRAZONE MOIETY AND THEIR USE IN DYE-SENSITIZED SOLAR CELLS

This application is a Continuation of U.S. Non-Provisional application Ser. No. 13/932,403, which was filed on Jul. 1, 2013. This application is based upon and claims the benefit of priority to U.S. Provisional Application No. 61/667,971, which was filed on Jul. 4, 2012, the entire contents of which are incorporated herein by reference.

The present invention relates to compounds of general formula I

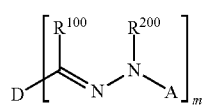

(I)

wherein $R^{100}$ and $R^{200}$ are each independently hydrogen, $C_1$-$C_{10}$-alkyl which in case of $C_2$-alkyl may be interrupted by one and in case of $C_3$-$C_{10}$-alkyl by one or two nonadjacent oxygen atoms, $C_5$-$C_7$-cycloalkyl, aryl, aryl-$C_1$-$C_{10}$-alkyl or aryloxy-$C_1$-$C_{10}$-alkyl, D is an m-valent (m=1, 2 or 3) donor moiety which comprises at least one carbon-carbon or carbon-heteroatom double bond and/or at least one unfused or fused carbo- or heterocyclic ring, A is an acceptor moiety which comprises at least one carbon-carbon or carbon-heteroatom double bond and/or at least one unfused or fused carbo- or heterocyclic ring, and the donor moiety D and the acceptor moiety A are π-conjugated to one another.

Furthermore, the present invention relates to the use of compounds of formula I for producing dye-sensitized solar cells and to dye-sensitized solar cells comprising compounds of formula I.

The direct conversion of solar energy to electrical energy in solar cells is based on the internal photoeffect of a semiconductor material, i.e. the generation of electron-hole pairs by absorption of photons and the separation of the negative and positive charge carriers at a p-n junction or a Schottky contact. The photovoltage thus generated can bring about a photocurrent in an external circuit, through which the solar cell delivers its power.

Thin layers or films of metal oxides are known to constitute inexpensive solid semiconductor materials (n-semiconductors), but their absorption, owing to large band gaps, is typically not within the visible region of the electromagnetic spectrum. For use in solar cells, the metal oxides therefore have to be combined with a photosensitizer which absorbs in the wavelength range of sunlight, i.e. at from 300 to 2000 nm, and, in the electronically excited state, injects electrons into the conduction band of the semiconductor. With the aid of a redox system which is used additionally in the cell and is reduced at the counterelectrode, electrons are recycled to the sensitizer which is thus regenerated.

Of particular interest for use in solar cells are the semiconductors zinc oxide, tin dioxide and especially titanium dioxide, which are used in the form of nanocrystalline porous layers. These layers have a large surface area which is coated with the sensitizer, so that high absorption of sunlight is achieved.

Dye-sensitized solar cells (DSCs) which are based on titanium dioxide as the semiconductor material are described, for example, in U.S. Pat. No. 4,927,721, Nature 353, p. 737-740 (1991) and U.S. Pat. No. 5,350,644, and also Nature 395, p. 583-585 (1998) and EP-A-1 176 646. These solar cells comprise monomolecular films of transition metal complexes, especially ruthenium complexes, which are bonded to the titanium dioxide layer via acid groups, as sensitizers and iodine/iodide redox systems present in dissolved form or amorphous organic p-conductors based on spirobifluorenes.

Ruthenium complexes as molecular sensitizers have shown impressive solar-to-electric power conversion efficiencies (PCE) in liquid electrolyte based devices, with the PCE reaching over 11% under standard AM1.5G full sunlight as was shown by M. K. Nazeeruddin, F. De Angelis, S. Fantacci, A. Selloni, G. Viscardi, P. Liska, S. Ito, T. Bessho, M. Grätzel, J. Am. Chem. Soc. 2005, 127, 16835;

Y. Chiba, A. Islam, Y. Watanabe, R. Komiya, N. Koide, L. Y. Han, Jpn. J. Appl. Phys. 2006, 45, L638;

F. Gao, Y. Wang, D. Shi, J. Zhang, M. K. Wang, X. Y. Jing, R. Humphry-Baker, P. Wang, S. M. Zakeeruddin, M. Grätzel, J. Am. Chem. Soc. 2008, 130, 10720;

Y. M. Cao, Y. Bai, Q. J. Yu, Y. M. Cheng, S. Liu, D. Shi, F. Gao, P. Wang, J. Phys. Chem. C 2009, 113, 6290; and C.-Y. Chen, M. K. Wang, J.-Y. Li, N. Pootrakuichote, L. Alibabaei, C. H. Ngoc-le, J. D. Decoppet, J. H. Tsai, C. Gratzel, C. G. Wu, S. M. Zakeeruddin, M. Grätzel, ACS Nano 2009, 3, 3103.

In recent years, metal-free organic dyes have attracted increasing attention as they do not contain any toxic or costly metal and their properties are easily tuned by facile structural modification. In addition, they generally have much higher extinction coefficients when compared to Ru(II) polypyridyls, making them excellent for use in solid state DSCs in combination with hole transporting materials such as P3HT as shown, for example, by G. K. Mor, S. Kim, M. Paulose, O. K. Varghese, K. Shankar, J. Basham and C. A. Grimes, Nano Lett., 2009, 9, 4250, or spiro-MeOTAD as shown, for example, by H. J. Snaith, A. J. Moule, C. Klein, K. Meerholz, R. H. Friend, M. Grätzel, Nano Lett., 2007, 7, 3372.

U.S. Pat. No. 6,359,211 describes cyanine, oxazine, thiazine and acridine dyes which have carboxyl groups bonded via an alkylene radical for securing to the titanium dioxide semiconductor.

Perylene-3,4:9,10-tetracarboxylic acid derivatives as sensitizers are examined in Japanese documents JP-A-10-189065, 2000-243463, 2001-093589, 2000-100484 and 10-334954, and in New J. Chem. 26, p. 1155-1160 (2002).

The most extensively examined metal-free sensitizers at present include dyes which possess a cyanoacrylate anchor group. For example, Kim, S.; Lee, J. K.; Kang, S. O.; Yum, J. H.; Fantacci, S.; DeAngelis, F.; Di Censo, D.; Nazeerruddin, M. K.; Grätzel, M. JACS 2006, 128, 16701 describes the compound

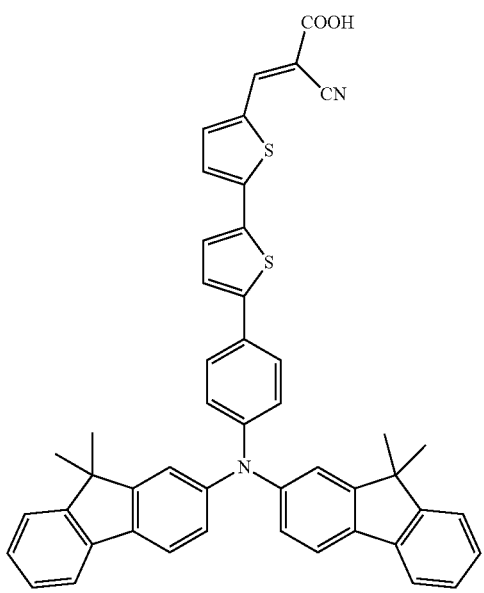

("JK2")

and Solar Energy Materials & Solar Cells 2009, 93, 1143 the compound

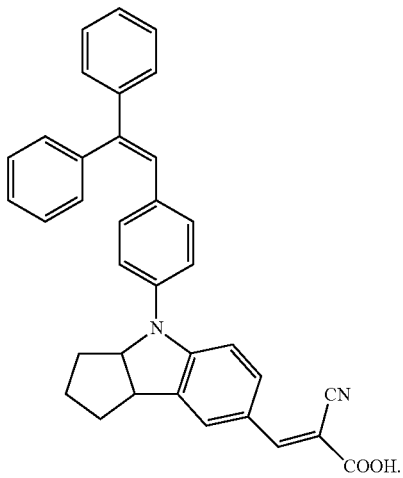 [SMILES: N#C/C(=C\c1ccc2c(c1)C1CCCC1N2c1ccc(C=C(c2ccccc2)c2ccccc2)cc1)C(=O)O]

Dyes with naphthalene monoimide anchor groups are described in the document WO 2008/132103 A1.

To date the most efficient metal-free organic dyes for DSCs are based upon the D-π-A (donor moiety—π-conjugation bridging moiety—acceptor moiety) architecture. With this construction it is possible to design new dye structures, extend the absorption spectra, adjust the energy levels and complete the intramolecular charge separation.

DSCs employing organic dyes featuring an electron donor and acceptor moiety connected by a π-conjugation bridge have reached ~10% efficiency with liquid electrolytes and up to 6% with solid HTM as shown for the former by K. Hara, T. Sato, R. Katoh, A. Furube, Y. Ohga, A. Shinpo, S. Suga, K. Sayama, H. Sugihara, H. Arakawa, J. Phys. Chem. B 2003, 107, 597;

T. Horiuchi, H. Miura, K. Sumioka, S. Uchida, J. Am. Chem. Soc. 2004, 126, 12218;

S. Kim, J. K. Lee, S. O. Kang, J. Ko, J.-H. Yum, S. Fantacci, F. De Angelis, D. Di Censo, M. K. Nazeeruddin, M. Grätzel, J. Am. Chem. Soc. 2006, 128, 16701;

D. P. Hagberg, T. Edvinsson, T. Marinado, G. Boschloo, A. Hagfeldt, L. C. Sun, Chem. Commun. 2006, 2245;

W. D. Zeng, Y. M. Cao, Y. Bai, Y. H. Wang, Y. S. Shi, M. Zhang, F. F. Wang, C. Y. Pan, P. Wang, Chem. Mater. 2010, 22, 1915.

and for the latter by

N. Cai, S.-J. Moon, L. Cevey-Ha, T. Moehl, R. Humphry-Baker, P. Wang, S. M. Zakeeruddin, M. Grätzel, Nano Lett. 2011, 11, 1452;

X. Liu, W. Zhang, S. Uchida, L. Cai, B. Liu, S. Ramakrishna, Adv. Mater. 2010, 22, E150.

A large variety of donors has been investigated, like tetrahydroquinoline, indoline, coumarin, triarylamine, heteroanthracene, carbazole, N, N-dialkylaniline, and fluorene derivatives. The majority of these dyes contain thiophene derivatives or ethenyl fragments of various length as π-conjugation bridges, as disclosed, for example, in A. Mishra, M. K. R. Fischer, P. Bäuerle, Angew. Chem. 2009, 121, 2510; A. Mishra, M. K. R. Fischer, P. Bäuerle Angew. Chem. Int. Ed. 2009, 48, 2474;

A. Hagfeldt, G. Boschloo, L. Sun, L. Kloo, H. Pettersson Chem. Rev. 2010, 110, 6595;

C. Li, M. Liu, N. G. Pschirer, M. Baumgarten, K. Müllen Chem. Rev., 2010, 110, 6817;

Y. Ooyama, Y. Harima Eur. J. Org. Chem. 2009, 2903.

Those bridging units are shown to be very effective; however, their synthesis often involves organotin, organolithium, or organomagnesium reagents, expensive palladium or nickel catalysts, rigorously anhydrous and oxygen-free conditions.

Hydrazone derivatives, on the other hand, are known for their low cost, simple synthesis, and rapid charge transporting ability, as shown by R. Lygaitis, V. Getautis, J. V. Grazulevicius, Chem. Soc. Rev. 2008, 37, 770.

Further dyes comprising hydrazone moieties are described in P. Shen, X. Liu, S. Jiang, Y. Huang, L. Yi, B. Zhao, S. Tan, Org. Electronics, 12 (2011), 1992-2002 and P. Shen, X. Liu, S. Jiang, L. Wang, L. Yi, D. Ye, B. Zhao, S. Tan, Dyes and Pigments, 92 (2012), 1042-1051. In these documents the hydrazone moieties, however, do not constitute the π-conjugation bridge but rather function as part of the donor moiety.

In view of the aforesaid it is the main object of the present invention to provide further efficient, metal-free organic dyes based upon the D-π-A architecture for the application in DSCs and, preferably, sDSCs which exhibit good to very good quantum efficiencies with very good medium to long term stabilities.

Accordingly, compounds of the formula I

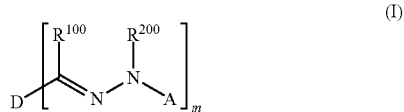

have been synthesized, wherein $R^{100}$ and $R^{200}$ mare each independently hydrogen, $C_1$-$C_{10}$-alkyl which in case of $C_2$-alkyl may be interrupted by one and in case of $C_3$-$C_{10}$-alkyl by one or two nonadjacent oxygen atoms, $C_5$-$C_7$-cycloalkyl, aryl, aryl-$C_1$-$C_{10}$-alkyl or aryloxy-$C_1$-$C_{10}$-alkyl, D is an m-valent donor moiety which comprises at least one carbon-carbon or carbon-heteroatom double bond and/or at least one unfused or fused carbo- or heterocyclic ring, A is an acceptor moiety which comprises at least one carbon-carbon or carbon-heteroatom double bond and/or at least one unfused or fused carbo- or heterocyclic ring, and the donor moiety D and the acceptor moiety A are π-conjugated to one another.

In the context of the present application $C_1$-$C_{10}$-alkyl should be understood to mean linear or branched alkyl, for example methyl, ethyl, n-propyl, isopropyl, n-butyl, isobutyl, sec-butyl, tert-butyl, n-pentyl, n-hexyl, n-heptyl, n-octyl, 2-ethylhexyl, n-nonyl and n-decyl. Preferred groups are methyl, isopropyl, n-butyl, tert-butyl and 2-ethylhexyl; in the radicals mentioned, it is optionally possible for one or more hydrogen atoms to be replaced by fluorine atoms, such that these radicals may also be partly fluorinated or perfluorinated.

$C_1$-$C_{10}$-Alkyl which in case of $C_2$-alkyl may be interrupted by one and in case of $C_3$-$C_{10}$-alkyl by one or two nonadjacent oxygen atoms is, for example, 3-methoxyethyl, 2- and 3-methoxypropyl, 2-ethoxyethyl, 2- and 3-ethoxypropyl, 2-propoxyethyl, 2- and 3-propoxypropyl, 2-butoxyethyl, 2- and 3-butoxypropyl, 3,6-dioxaheptyl and 3,6-dioxaoctyl.

The $C_1$-$C_{10}$-alkoxy, $C_1$-$C_{10}$-alkylamino-, di($C_1$-$C_{10}$-alkyl)amino, $C_1$-$C_{10}$-alkylamino-sulfonylamino-, di($C_1$-$C_{10}$-alkyl)aminosulfonylamino and $C_1$-$C_{10}$-alkylsulfonylamino radicals are correspondingly derived from the aforementioned $C_1$-$C_{10}$-alkyl radicals, where, in the case of the di($C_1$-$C_{10}$-alkyl)amino groups, either identical or different $C_1$-$C_{10}$-alkyl radicals may be present on the amino group. Examples include methoxy, ethoxy, n-propoxy, isopropoxy, n-butoxy, isbutoxy, sec-butoxy, tert-butoxy, n-pentoxy, n-hexoxy, n-heptoxy, n-octoxy, 2-ethylhexoxy, n-nonoxy and n-decoxy, methylamino, ethylamino, n-propylamino, isopropylamino, n-butylamino, isobutylamino, sec-butylamino, tert-butylamino, n-pentylamino, n-hexylamino, n-heptylamino, n-octyl-amino, 2-ethylhexylamino, n-nonylamino and n-decylamino, dimethylamino, diethyl-amino, di(n-propyl)amino, diisopropylamino, di(n-butyl)amino, diisobutylamino, di(sec-butyl)amino, di(tert-butyl)amino, di(n-pentyl)amino, di(n-hexyl)amino, di(n-heptyl)amino, di(n-octyl)amino, di(2-ethylhexyl)amino, di(n-nonyl)amino and di(n-decyl)amino, and also the corresponding mixed dialkylamino radicals, for instance methylethylamino to methyl-n-decylamino, ethyl-n-propylamino to ethyl-n-decylamino, etc., and also methyl-aminosulfonylamino, ethylaminosulfonylamino, n-propyl-aminosulfonylamino, isopropyl-aminosulfonylamino, n-butylaminosulfonylamino, isobutylaminosulfonylamino, sec-butylaminosulfonylamino, tert-butylaminosulfonylamino, n-pentylaminosulfonylamino, n-hexylaminosulfonylamino, n-heptylaminosulfonylamino, n-octylaminosulfonylamino, 2-ethylhexylaminosulfonyl-amino, n-nonylaminosulfonylamino and n-decylaminosulfonylamino, dimethylaminosulfonylamino, diethylaminosulfonylamino, di(n-propyl)amino-sulfonylamino, diisopropylaminosulfonylamino, di(n-butyl)aminosulfonylamino, diiso-butylaminosulfonylamino, di(sec-butyl)amino-sulfonylamino, di(tert-butyl)amino-sulfonylamino, di(n-pentyl)aminosulfonylamino, di(n-hexyl)aminosulfonylamino, di(n-heptyl)aminosulfonylamino, di(n-octyl)aminosulfonylamino, di(2-ethylhexyl)amino-sulfonylamino, di(n-nonyl)amino-sulfonylamino and di(n-decyl)aminosulfonylamino, and also the corresponding radicals comprising mixed dialkylamino radicals, for instance methylethylaminosulfonylamino to methyl-n-decylaminosulfonylamino, ethyl-n-propyl-aminosulfonylamino to ethyl-n-decylaminosulfonylamino etc., up to n-nonyl-n-decylaminosulfonylamino, and also methylsulfonylamino, ethylsulfonylamino, n-propyl-sulfonylamino, isopropylsulfonylamino, n-butylsulfonylamino, isobutylsulfonylamino, sec-butylsulfonylamino, tert-butylsulfonylamino, n-pentylsulfonylamino, n-hexylsulfonyl-amino, n-heptylsulfonylamino, n-octylsulfonylamino, 2-ethylhexylsulfonylamino, n-nonylsulfonylamino and n-decylsulfonylamino.

$C_5$-$C_1$-Cycloalkyl is understood to mean especially cyclopentyl, cyclohexyl and cycloheptyl.

In the context of the present invention, aryl is an aryl radical, aryl unit or aryl group especially with a base skeleton of 6 to 30 carbon atoms, preferably 6 to 18 carbon atoms, and comprises mono- or polycyclic aromatic hydrocarbon radicals which may be unsubstituted or substituted. Aryl is preferably phenyl, tolyl, xylyl, mesityl, duryl, naphthyl, quinolinyl, fluorenyl, carbazolyl, anthracenyl, phenanthrenyl, stilbyl, 4(2,2-diphenylethenyl)phenyl or naphthyl, more preferably phenyl or naphthyl, where these aryl groups, in the case of substitution, may bear generally 1, 2, 3, 4 or 5, preferably 1, 2 or 3, substituents which are selected from the group of radicals consisting of halogen, $C_1$-$C_{10}$-alkyl, $C_1$-$C_{10}$-alkoxy, cyano, nitro, —C($R^a$)=N—N$R^a R^b$, —SO$_2$N$R^a R^b$, —NHSO$_2$N$R^a R^b$, —CON$R^a R^b$ and —CO$_2 R^a$, where the $C_1$-$C_{10}$-alkoxy groups derive from the $C_1$-$C_{10}$-alkyl groups listed above. $R^a$ and $R^b$ are preferably each independently hydrogen, aryl, preferably phenyl, or $C_1$-$C_{10}$-alkyl which in case of $C_2$-alkyl may be interrupted by one and in case of $C_3$-$C_{10}$-alkyl by one or two nonadjacent oxygen atoms.

The aryl-$C_1$-$C_{10}$-alkyl and aryloxy-$C_1$-$C_{10}$-alkyl groups derive from the alkyl and aryl groups listed above by formal replacement of one hydrogen atom of the linear or branched alkyl chain by an aryl or aryloxy group. Preferred groups here are benzyl and linear aryloxy-$C_1$-$C_{10}$-alkyl, where, in the case of $C_2$-$C_{10}$-alkyl radicals, the aryloxy radical is preferably bonded terminally.

In the context of the present invention, alkali metal cation as the definition of M is preferably lithium, sodium, cesium or potassium, more preferably sodium.

In the context of the present invention, halogen denotes fluorine, chlorine, bromine or iodine, especially fluorine and chlorine.

Preference is given to compounds of formula I wherein in general formula I $R^{100}$ is hydrogen or $C_1$-$C_4$-alkyl and $R^{200}$ is aryl or $C_1$-$C_{10}$-alkyl which in case of $C_2$-alkyl may be interrupted by one and in case of $C_3$-$C_{10}$-alkyl by one or two nonadjacent oxygen atoms.

Further preference, also with reference to the aforementioned preference, is given to compounds, wherein the donor moiety D in general formula I for m=1:

is selected from the group consisting of

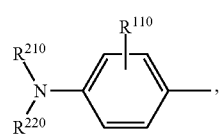
(D01)

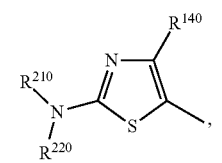
(D02)

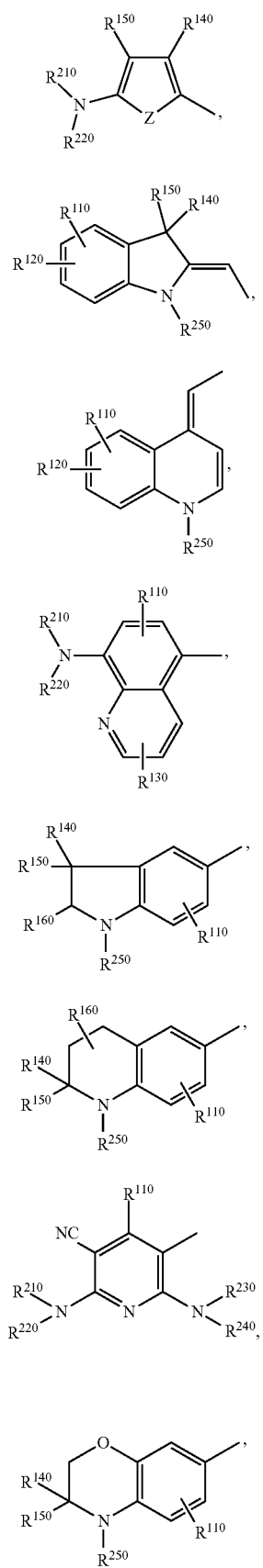

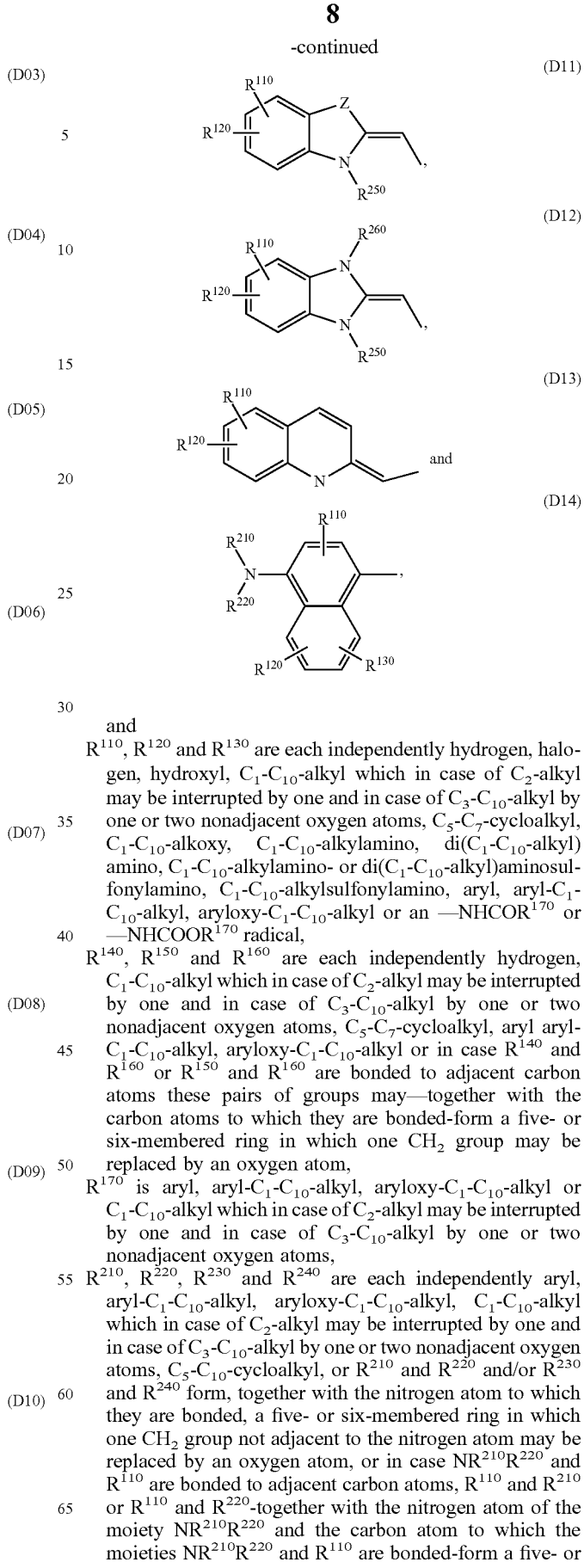

and $R^{110}$, $R^{120}$ and $R^{130}$ are each independently hydrogen, halogen, hydroxyl, $C_1$-$C_{10}$-alkyl which in case of $C_2$-alkyl may be interrupted by one and in case of $C_3$-$C_{10}$-alkyl by one or two nonadjacent oxygen atoms, $C_5$-$C_7$-cycloalkyl, $C_1$-$C_{10}$-alkoxy, $C_1$-$C_{10}$-alkylamino, di($C_1$-$C_{10}$-alkyl)amino, $C_1$-$C_{10}$-alkylamino- or di($C_1$-$C_{10}$-alkyl)aminosulfonylamino, $C_1$-$C_{10}$-alkylsulfonylamino, aryl, aryl-$C_1$-$C_{10}$-alkyl, aryloxy-$C_1$-$C_{10}$-alkyl or an —NHCOR$^{170}$ or —NHCOOR$^{170}$ radical, $R^{140}$, $R^{150}$ and $R^{160}$ are each independently hydrogen, $C_1$-$C_{10}$-alkyl which in case of $C_2$-alkyl may be interrupted by one and in case of $C_3$-$C_{10}$-alkyl by one or two nonadjacent oxygen atoms, $C_5$-$C_7$-cycloalkyl, aryl aryl-$C_1$-$C_{10}$-alkyl, aryloxy-$C_1$-$C_{10}$-alkyl or in case $R^{140}$ and $R^{160}$ or $R^{150}$ and $R^{160}$ are bonded to adjacent carbon atoms these pairs of groups may—together with the carbon atoms to which they are bonded-form a five- or six-membered ring in which one $CH_2$ group may be replaced by an oxygen atom, $R^{170}$ is aryl, aryl-$C_1$-$C_{10}$-alkyl, aryloxy-$C_1$-$C_{10}$-alkyl or $C_1$-$C_{10}$-alkyl which in case of $C_2$-alkyl may be interrupted by one and in case of $C_3$-$C_{10}$-alkyl by one or two nonadjacent oxygen atoms, $R^{210}$, $R^{220}$, $R^{230}$ and $R^{240}$ are each independently aryl, aryl-$C_1$-$C_{10}$-alkyl, aryloxy-$C_1$-$C_{10}$-alkyl, $C_1$-$C_{10}$-alkyl which in case of $C_2$-alkyl may be interrupted by one and in case of $C_3$-$C_{10}$-alkyl by one or two nonadjacent oxygen atoms, $C_5$-$C_{10}$-cycloalkyl, or $R^{210}$ and $R^{220}$ and/or $R^{230}$ and $R^{240}$ form, together with the nitrogen atom to which they are bonded, a five- or six-membered ring in which one $CH_2$ group not adjacent to the nitrogen atom may be replaced by an oxygen atom, or in case $NR^{210}R^{220}$ and $R^{110}$ are bonded to adjacent carbon atoms, $R^{110}$ and $R^{210}$ or $R^{110}$ and $R^{220}$-together with the nitrogen atom of the moiety $NR^{210}R^{220}$ and the carbon atom to which the moieties $NR^{210}R^{220}$ and $R^{110}$ are bonded-form a five- or six-membered ring in which one $CH_2$ group not adjacent to the nitrogen atom may be replaced by an oxygen atom and which five- or six-membered ring may be fused to another five- or six-membered saturated or unsaturated ring, $R^{250}$ and $R^{260}$ are each independently $C_1$-$C_{10}$-alkyl which in case of $C_2$-alkyl may be interrupted by one and in case of $C_3$-$C_{10}$-alkyl by one or two nonadjacent oxygen atoms, $C_5$-$C_7$-cycloalkyl, aryl, aryl-$C_1$-$C_{10}$-alkyl or aryloxy-$C_1$-$C_{10}$-alkyl and Z is O or S, for m=2:

is selected from the group consisting of:

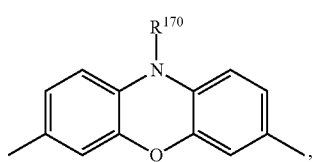

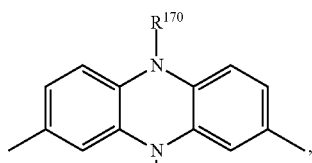

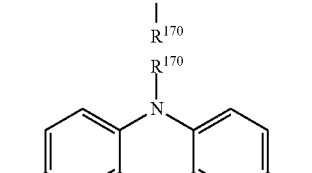

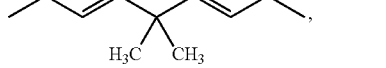

and

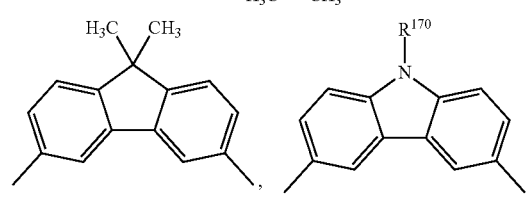

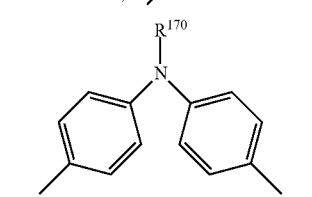

where $R^{170}$ has the meaning given before and in case of two moities may vary independently of each other, and for m=3:

is selected from the group consisting of:

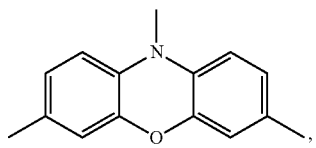

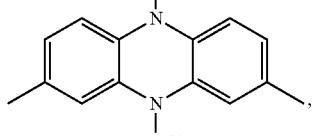

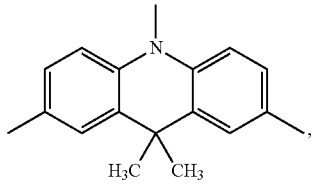

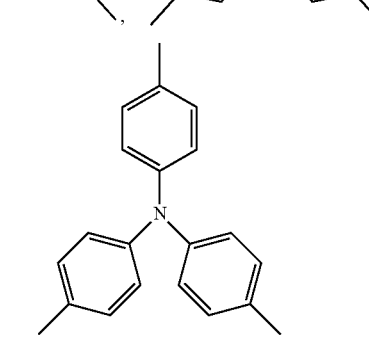

and

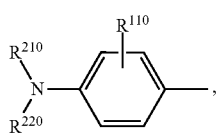

where $R^{170}$ has the meaning given before.

Further preference, also with reference to the aforementioned preference with respect to $R^{100}$ and $R^{200}$, is given to compounds, wherein the donor moiety D in general formula I for m=1:

is selected from the group consisting of:

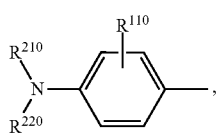
(D01)

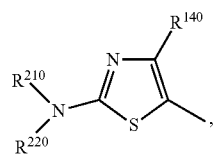
(D02)

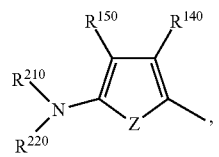
(D03)

-continued (D06)
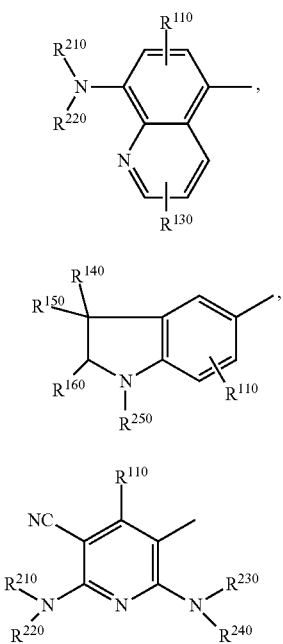

for m=2:
is selected from the group consisting of:

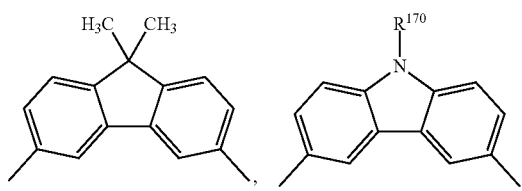

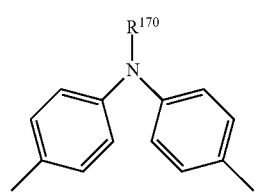

and for m=3:
is selected from the group consisting of:

(D07)
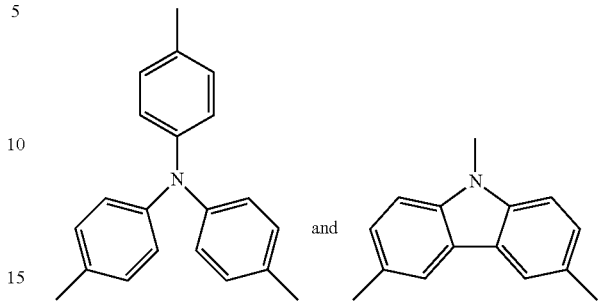

and the variables have the aforementioned meaning.

(D09) Particular preference, also with reference to the aforementioned preference with respect to $R^{100}$ and $R^{200}$, is given to compounds, wherein the donor moiety D in general formula I for m=1:
is a moiety:

(D14)

(D01)
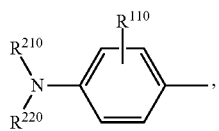

and $R^{110}$ is hydrogen, halogen, hydroxyl, $C_1$-$C_{10}$-alkyl which in case of $C_2$-alkyl may be interrupted by one and in case of $C_3$-$C_{10}$-alkyl by one or two nonadjacent oxygen atoms, $C_5$-$C_7$-cycloalkyl, $C_1$-$C_{10}$-alkoxy, $C_1$-$C_{10}$-alkylamino, di($C_1$-$C_{10}$-alkyl)amino, $C_1$-$C_{10}$-alkylamino- or di($C_1$-$C_{10}$-alkyl)aminosulfonylamino, $C_1$-$C_{10}$-alkylsulfonylamino, aryl, aryl-$C_1$-$C_{10}$-alkyl, aryloxy-$C_1$-$C_{10}$-alkyl or an —NHCOR$^{170}$ or —NHCOOR$^{170}$ radical, $R^{170}$ is aryl, aryl-$C_1$-$C_{10}$-alkyl, aryloxy-$C_1$-$C_{10}$-alkyl or $C_1$-$C_{10}$-alkyl which in case of $C_2$-alkyl may be interrupted by one and in case of $C_3$-$C_{10}$-alkyl by one or two nonadjacent oxygen atoms, and $R^{210}$ and $R^{220}$ are each independently aryl, aryl-$C_1$-$C_{10}$-alkyl, aryloxy-$C_1$-$C_{10}$-alkyl, $C_1$-$C_{10}$-alkyl which in case of $C_2$-alkyl may be interrupted by one and in case of $C_3$-$C_{10}$-alkyl by one or two nonadjacent oxygen atoms, $C_5$-$C_{10}$-cycloalkyl, or $R^{210}$ and $R^{220}$ form, together with the nitrogen atom to which they are bonded, a five- or six-membered ring in which one $CH_2$ group not adjacent to the nitrogen atom may be replaced by an oxygen atom, or in case NR$^{210}$R$^{220}$ and $R^{110}$ are bonded to adjacent carbon atoms, $R^{110}$ and $R^{210}$ or $R^{110}$ and $R^{220}$-together with the nitrogen atom of the moiety NR$^{210}$R$^{220}$ and the carbon atom to which the moieties NR$^{210}$R$^{220}$ and $R^{110}$ are bonded-form a five- or six-membered ring in which one $CH_2$ group not adjacent to the nitrogen atom may be replaced by an oxygen atom and which five- or six-membered ring may be fused to another five- or six-membered saturated or unsaturated ring, for m=2:
is selected from the group consisting of:

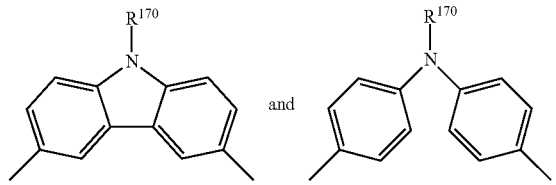

where $R^{170}$ has the meaning given before,
and for m=3:
is a moiety

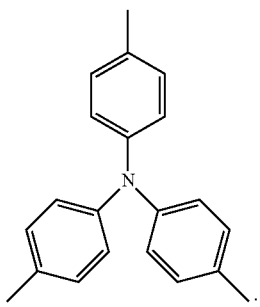

Further preference, also with reference to the aforementioned preferences with respect to the donor moiety D and $R^{100}$ and $R^{200}$, is given to compounds, wherein the acceptor moiety A in general formula I is a group of formula Ia:

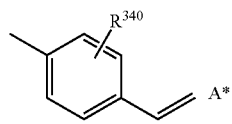 (Ia)

wherein A* denotes a moiety selected from the group consisting of

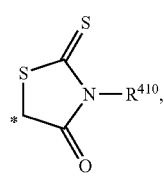 (A01)

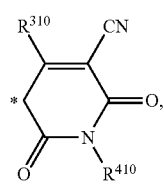 (A02)

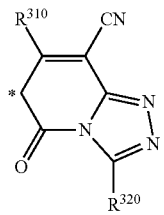 (A03)

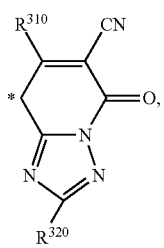 (A04)

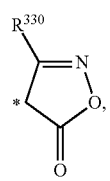 (A05)

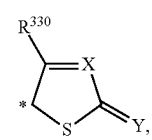 (A06)

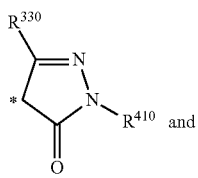 (A07)

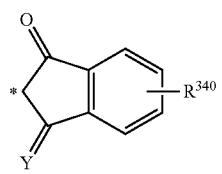 (A08)

and
* indicates the position which the double bond of the group of formula Ia is bonded to,
$R^{310}$ and $R^{320}$ are each independently hydrogen, $C_1$-$C_{10}$-alkyl which in case of $C_2$-alkyl may be interrupted by one and in case of $C_3$-$C_{10}$-alkyl by one or two nonadjacent oxygen atoms, or $C_5$-$C_7$-cycloalkyl,
$R^{330}$ is hydrogen, $C_1$-$C_{10}$-alkyl which in case of $C_2$-alkyl may be interrupted by one and in case of $C_3$-$C_{10}$-alkyl by one or two nonadjacent oxygen atoms, partly fluorinated $C_1$-$C_{10}$-alkyl, perfluorinated $C_1$-$C_{10}$-alkyl, $C_5$-$C_7$-cycloalkyl, aryl, aryl-$C_1$-$C_{10}$-alkyl or aryloxy-$C_1$-$C_{10}$-alkyl,
$R^{340}$ is hydrogen, $NO_2$, CN, $COR^{350}$, $COOR^{350}$, $SO_2R^{350}$ or $SO_3R^{350}$,
$R^{350}$ is aryl, aryl-$C_1$-$C_{10}$-alkyl, aryloxy-$C_1$-$C_{10}$-alkyl or $C_1$-$C_{10}$-alkyl which in case of $C_2$-alkyl may be interrupted by one and in case of $C_3$-$C_{10}$-alkyl by one or two nonadjacent oxygen atoms,
$R^{410}$ is hydrogen, $C_1$-$C_{10}$-alkyl which in case of $C_2$-alkyl may be interrupted by one and in case of $C_3$-$C_{10}$-alkyl by one or two nonadjacent oxygen atoms and which may be mono- or polysubstituted by hydroxyl, mercapto, halogen, cyano, nitro, —COOM and/or —COOR$^{420}$, C$_5$-C$_7$-cycloalkyl, aryl, aryl-C$_1$-C$_{10}$-alkyl, aryloxy-C$_1$-C$_{10}$-alkyl, or an —NHCOR$^{420}$ or —N(COR$^{420}$)$_2$) radical where the two R$^{420}$ in the latter may be the same or different, X is independently CH or N, Y is O, C(CN)$_2$, C(CN)(COOM) or C(CN)(COOR$^{420}$), M is alkali metal cation or [NR$^{420}$]$_4{}^+$, and R$^{420}$ is hydrogen, aryl, aryl-C$_1$-C$_{10}$-alkyl, aryloxy-C$_1$-C$_{10}$-alkyl or C$_1$-C$_{10}$-alkyl which in case of C$_2$-alkyl may be interrupted by one and in case of C$_3$-C$_{10}$-alkyl by one or two nonadjacent oxygen atoms.

Further preference, also with reference to the aforementioned preferences with respect to the donor moiety D and R$^{100}$ and R$^{200}$, is given to compounds, wherein the acceptor moiety A in general formula I is:

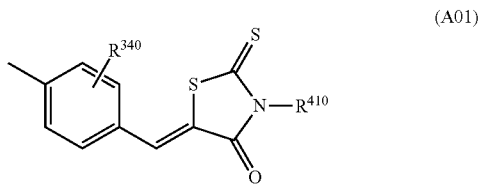

(A01)

and

R$^{340}$ is hydrogen, NO$_2$, CN, COR$^{350}$, COOR$^{350}$, SO$_2$R$^{350}$ or SO$_3$R$^{350}$, R$^{350}$ is aryl, aryl-C$_1$-C$_{10}$-alkyl, aryloxy-C$_1$-C$_{10}$-alkyl or C$_1$-C$_{10}$-alkyl which in case of C$_2$-alkyl may be interrupted by one and in case of C$_3$-C$_{10}$-alkyl by one or two nonadjacent oxygen atoms, R$^{410}$ is hydrogen, C$_1$-C$_{10}$-alkyl which in case of C$_2$-alkyl may be interrupted by one and in case of C$_3$-C$_{10}$-alkyl by one or two nonadjacent oxygen atoms and which may be mono- or polysubstituted by hydroxyl, mercapto, halogen, cyano, nitro, —COOM and/or —COOR$^{420}$, C$_5$-C$_7$-cycloalkyl, aryl, aryl-C$_1$-C$_{10}$-alkyl, aryloxy-C$_1$-C$_{10}$-alkyl, or an —NHCOR$^{420}$ or —N(COR$^{420}$)$_2$ radical where the two R$^{420}$ in the latter may be the same or different, M is alkali metal cation or [NR$^{420}$]$_4{}^+$, and R$^{420}$ is hydrogen, aryl, aryl-C$_1$-C$_{10}$-alkyl, aryloxy-C$_1$-C$_{10}$-alkyl or C$_1$-C$_{10}$-alkyl which in case of C$_2$-alkyl may be interrupted by one and in case of C$_3$-C$_{10}$-alkyl by one or two nonadjacent oxygen atoms.

Particular preference, also with reference to the aforementioned preferences with respect to the donor moiety D and R$^{100}$ and R$^{200}$, is given to compounds wherein the acceptor moiety A in general formula I is:

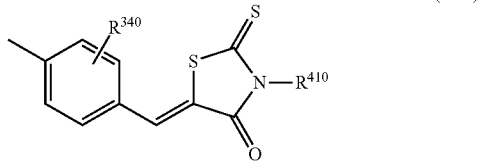

(A01)

and

R$^{340}$ is hydrogen, NO$_2$, CN, COR$^{350}$, COOR$^{350}$, SO$_2$R$^{350}$ or SO$_3$R$^{350}$, R$^{350}$ is aryl, aryl-C$_1$-C$_{10}$-alkyl, aryloxy-C$_1$-C$_{10}$-alkyl or C$_1$-C$_{10}$-alkyl which in case of C$_2$-alkyl may be interrupted by one and in case of C$_3$-C$_{10}$-alkyl by one or two nonadjacent oxygen atoms, R$^{410}$ is aryl or C$_1$-C$_{10}$-alkyl which in case of C$_2$-alkyl may be interrupted by one and in case of C$_3$-C$_{10}$-alkyl by one or two nonadjacent oxygen atoms and which is terminally substituted by hydroxyl, —COOM or —COOR$^{420}$, M is alkali metal cation or [NR$^{420}$]$_4{}^+$, and R$^{420}$ is hydrogen or C$_1$-C$_{10}$-alkyl which in case of C$_2$-alkyl may be interrupted by one and in case of C$_3$-C$_{10}$-alkyl by one or two nonadjacent oxygen atoms.

As a result of the preparation, it is possible in the individual case that a compound shown explicitly is not obtained, but rather an isomeric compound thereof, or that mixtures of isomers are also obtained. According to the invention, the isomeric compounds of the general formula I or the isomers of the corresponding preferred and particularly preferred compounds of general formula I, and also mixtures of isomers, shall accordingly also be comprised.

The preparation of the compounds of general formula I follows well established routes known to the person skilled in the art. Typically, donor moieties D with m aldehyde functions (m=1, 2 or 3) are reacted with a hydrazine derivative or formula

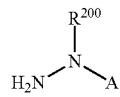

to deliver the desired hydrazones.

For preferred compounds comprising acceptor moieties A of formula Ia

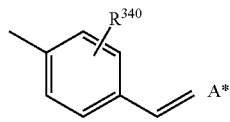

(Ia)

a favorable route comprises reacting fluoro-benzaldehyde with the hydrazone according to the scheme

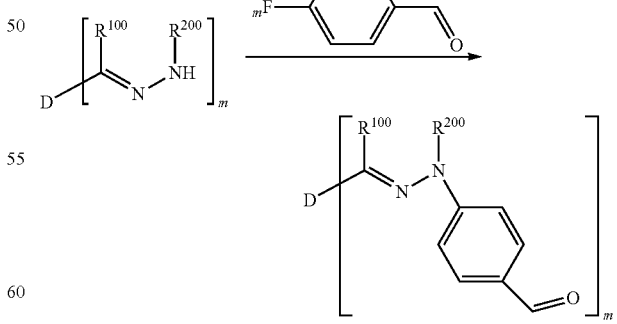

and further reacting the resulting aldehyde with the C—H acidic compounds underlying the moieties A*.

With respect to the exemplified A* moieties A01 to A08 above these educt compounds are (in the same order):

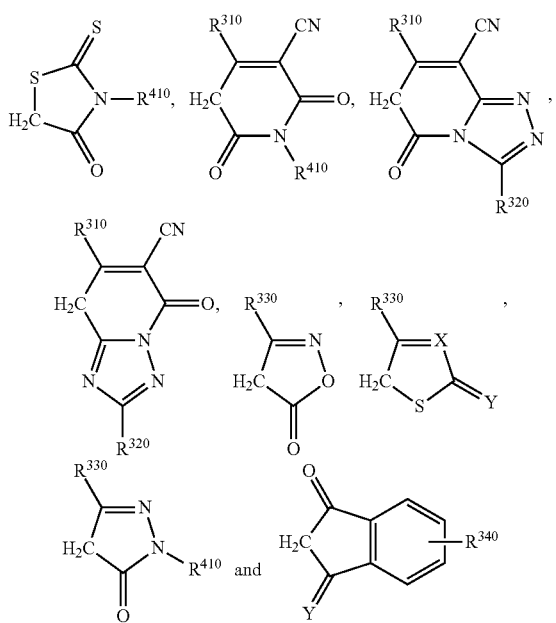

Further details on the preparation of the compounds according to the instant invention can be taken from the experimental section.

Also claimed in the context of the present invention is the use of compounds of formula I and their aforementioned preferences for producing dye-sensitized solar cells.

Further claimed according to the instant invention is a dye-sensitized solar cell comprising compounds of formula I and their aforementioned preferences.

DSCs generally comprise the following elements: an electrically conductive layer (being part of or forming the working electrode or anode), a photosensitive layer generally comprising a semi-conductive metal oxide and a photosensitive dye, a charge transfer layer and another electrically conductive layer (being part of or forming the counter electrode or cathode).

Regarding further details of the construction of sDSCs particular reference is made to WO 2012/001628 A1, which is hereby fully incorporated by reference.

EXPERIMENTAL PART

A) Preparation of Compounds According to the Invention

Materials and Methods

Chemicals were purchased from Aldrich and TCI Europe and used as received without further purification. 2-Iodofluorene (S. H. Lee, T. Nakamura, T. Tsutsui, Org. Lett. 2001, 3, 2005), 9,9-dimethyl-2-iodofluorene (C. H. Huang, S. H. Yang, K. B. Chen, C. S. Hsu, J. Polym. Sci. Part A: Polym. Chem. 2006, 44, 519), and N,N-bis(9,9-dimethylfluoren-2-yl)aniline (H. Doi, M. Kinoshita, K. Okumoto, Y. Shirota, Chem. Mater. 2003, 15, 1080) were synthesized according to the citations in parentheses, 4-[bis(4-methylphenyl)-amino]benzaldehyde was purchased from TCI Europe.

The $^1$H and $^{13}$C NMR spectra were taken on Varian Unity Inova (300 MHz) spectrometer at room temperature. All the data are given as chemical shifts in δ (ppm), $(CH_3)_4Si$ (TMS, 0 ppm) was used as an internal standard. The course of the reactions products were monitored by TLC on ALUGRAM SIL G/UV254 plates and developed with $I_2$ or UV light. Silica gel (grade 9385, 230-400 mesh, 60 Å, Aldrich) was used for column chromatography. Elemental analysis was performed with an Exeter Analytical CE-440 Elemental. IR-spectroscopy was performed on a Perkin Elmer Spectrum BX II FT-IR System, using KBr pellets. Mass spectra (MS) were recorded on an Aligent 110 (series MS with VL) apparatus. The UV spectra were recorded on a Perkin Elmer Lambda 35 spectrometer. $10^{-4}$ M solution of investigated dye in $CHCl_3$ and microcell with an internal width of 1 mm was used.

A1) Preparation of Dyes D1 to D9

Generalized Procedure

Condensation of the aldehyde 1 with phenyl hydrazine yielded hydrazone 2

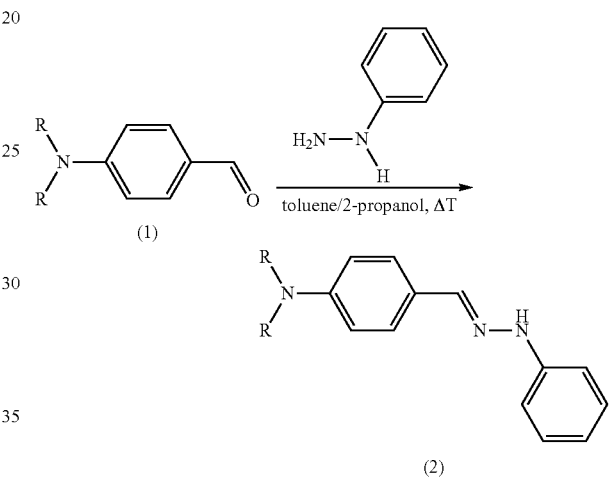

which was used in the arylation reaction with 4-fluorobenzaldehyde to yield compound 3 according to Route A)

Route A)

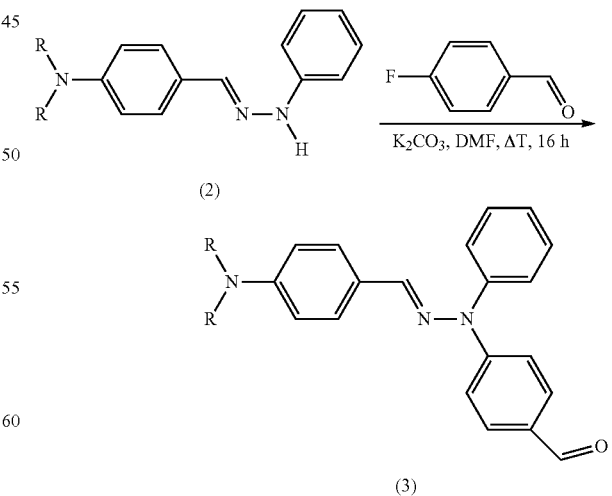

or alkylation reaction with 1-bromopropane and formylation of the alkylated intermediate 4 by the Vilsmeier-Haack method to yield compound 5 according to route B)

Route B)

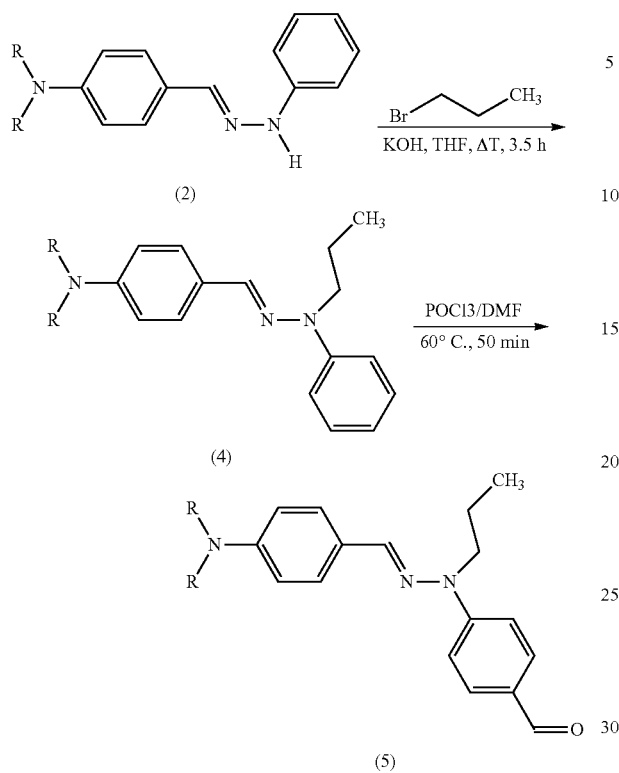

Finally, condensation of the aldehydes 3 and 5 with rhodanine-3-acetic acid yielded dyes ID-1276 (D1), ID-1261 (D2), ID-1300 (D3), ID-1332 (D4), ID-1464 (D5) and ID-1509 (D7) and with rhodanine-3-benzoic acid dye ID-1465 (D6), respectively. The variables R in the reaction routes shown before can be taken explicitly from the specific synthetic procedures.

Preparation of Dye D1

4-(4,4'-dimethyldiphenylamino)benzaldehyde-N-4-(3-carboxymethyl-4-oxo-2-thioxo-1,3-thiazolidin-5-ylidenmethyl)phenyl-N-phenylhydrazone

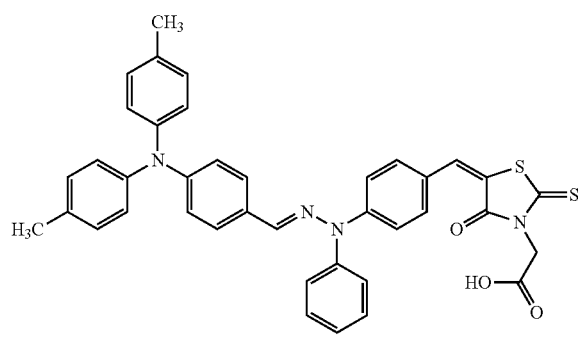 [SMILES: Cc1ccc(N(c2ccc(C)cc2)c2ccc(/C=N/N(c3ccccc3)c3ccc(/C=C4/SC(=S)N(CC(=O)O)C4=O)cc3)cc2)cc1]

A mixture of compound 3 (0.76 g, 1.54 mmol; both radicals R equal 4-methylphenyl), rhodanine-3-acetic acid (0.35 g, 1.85 mmol) and ammonium acetate (0.03 g, 0.46 mmol) was refluxed in acetic acid (5.0 mL) for 3 h. Afterwards, water (15 mL) was added and the extraction was done with chloroform. The organic layer was dried over anhydrous $Na_2SO_4$, filtered, and solvent evaporated. The crude product was purified by column chromatography using 7:18 v/v acetone/hexane followed by 7:1:17 v/v acetone/methanol/toluene as an eluent to collect dye D1 as a dark red solid (0.46 g, 45%).

$^1$H NMR (300 MHz, DMSO-$d_6$, δ): 7.94-6.69 (m, 24H), 4.58 (s, 2H, $CH_2$), 2.26 (s, 6H, $CH_3$);

$^{13}$C NMR (75 MHz, DMSO-$d_6$, δ): 193.48, 168.34, 167.39, 150.98, 149.43, 146.87, 144.85, 143.57, 138.39, 135.38, 133.69, 131.15, 130.85, 128.27, 126.27, 126.89, 125.59, 121.12, 119.08, 117.87, 115.36, 47.02, 30.32, 21.15;

IR (KBr): ν=3486 (OH); 3025 (aromatic CH); 2977, 2918, 2859 (aliphatic CH); 1708 (C=O); 1575, 1504 (C=C); 1294 (C=S); 1198, 1175, 1105 (C—N); 863, 815 (CH=CH of 1,4-disubstituted benzenes), 781, 745, 718 (CH=CH of monosubstituted benzene);

Anal. calcd for $C_{36}H_{32}N_4O_3S_2$(%): C, 70.04; H, 4.82; N, 8.38. found: C, 70.19; H, 4.88; N, 8.17.

Preparation of Dye D2 a) 4-(4,4'-dimethyldiphenylamino)benzaldehyde-N-phenyl-N-propylhydrazone (D2-1; corresponds to compound 4 where both radicals R equal 4-methylphenyl)

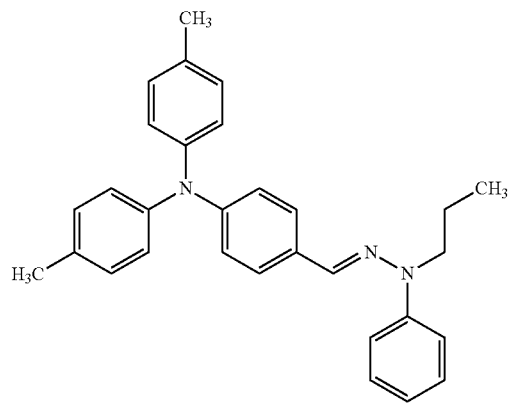 [SMILES: CCCN(/N=C/c1ccc(N(c2ccc(C)cc2)c2ccc(C)cc2)cc1)c1ccccc1]

To a refluxing mixture of compound 2 (1.45 g, 3.70 mmol; both radicals R equal 4-methylphenyl), dissolved in mixture of anhydrous tetrahydrofuran (3 mL) and 1-bromopropane (1 mL), powdered KOH (0.62 g, 11.11 mmol) and anhydrous $Na_2SO_4$ (0.21 g, 1.48 mmol) were added in three equal portions every 1 h. After 3.5 hours the reaction mixture was extracted with ethyl acetate and distilled water until neutral. The organic layer was dried over anhydrous $Na_2SO_4$, filtered off and ethyl acetate was removed. The residue was washed with a mixture of 2-propanol and n-hexane (1:1) to give compound D2-1 as yellow solid (1.53 g, 96%).

$^1$H NMR (300 MHz, $CDCl_3$, δ): 7.52 (d, J=8.6 Hz, 2H), 7.36 (s, 1H), 7.36-7.20 (m, 4H), 7.09-6.95 (m, 10H), 6.91-6.83 (m, 1H), 3.83 (t, J=7.7 Hz, 2H), 2.30 (s, 6H), 1.78-1.62 (m, 2H), 1.02 (t, J=7.3 Hz, 3H);

$^{13}$C NMR (75 MHz, $CDCl_3$, δ): 147.83, 147.28, 145.09, 132.55, 131.07, 130.22, 129.84, 128.99, 126.71, 124.62, 122.45, 119.82, 114.41, 46.77, 20.80, 18.28, 11.35;

Anal. calcd for $C_{30}H_{31}N_3$(%): C, 83.10; H, 7.21; N, 9.69. found: C, 83.33; H, 7.10; N, 9.57.

b) 4-(4,4'-dimethyldiphenylamino)benzaldehyde-N-(4-formyl)phenyl-N-propylhydrazone (D2-2)

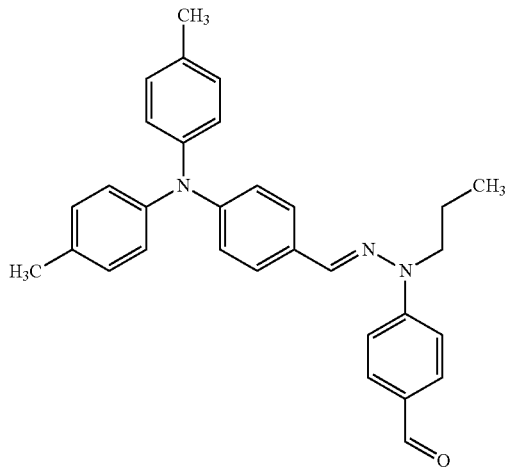 [SMILES: CCCN(/N=C/c1ccc(N(c2ccc(C)cc2)c2ccc(C)cc2)cc1)c1ccc(C=O)cc1]

Phosphorus oxychloride (0.16 mL, 1.73 mmol) was added dropwise to DMF (0.85 mL, 11.04 mmol), not allowing the temperature of the mixture to rise above 5° C. A solution of 17 (0.50 g, 1.15 mmol) in DMF (2.15 mL) was added, and the resulting mixture was heated at 60° C. for 30 min. The hot reaction mixture was poured into the ice-water, neutralized by adding sodium acetate (0.42 g, 5.19 mmol) aqueous solution, and extracted with ethyl acetate. The organic layer was dried over anhydrous $Na_2SO_4$, filtered, and solvent evaporated. The crude product was purified by column chromatography using 1.5:2:20 v/v acetone/diethyl ether/hexane as an eluent to collect compound D2-2 as a yellow solid (0.18 g, 34%).

$^1$H NMR (300 MHz, $CDCl_3$, δ): 9.82 (s, 1H, CHO), 7.79 (d, J=9.0 Hz, 2H), 7.62 (s, 1H), 7.55 (d, J=8.8 Hz, 2H), 7.41 (d, J=8.8 Hz, 2H), 7.12-6.96 (m, 10H), 3.90 (t, J=7.8 Hz, 2H, C$\underline{H}_2$CH$_2$CH$_3$), 2.32 (s, 6H, $CH_3$), 1.81-1.66 (m, 2H, $CH_2$C$\underline{H}_2$CH$_3$), 1.05 (t, J=7.3 Hz, 3H, $CH_2CH_2CH_3$);

$^{13}$C NMR (75 MHz, $CDCl_3$, δ): 190.65, 151.55, 148.89, 144.77, 134.97, 133.15, 131.62, 129.95, 128.55, 128.18, 127.37, 125.01, 121.67, 113.27, 45.94, 20.83, 18.48, 11.27;

Anal. calcd for $C_{31}H_3N_3O$ (%): C, 80.66; H, 6.77; N, 9.10. found: C, 80.53; H, 6.90; N, 9.02.

c) 4-(4,4'-dimethyldiphenylamino)benzaldehyde-N-4-(3-carboxymethyl-4-oxo-2-thioxo-1,3-thiazolidin-5-ylidenmethyl)phenyl-N-propylhydrazone (D2)

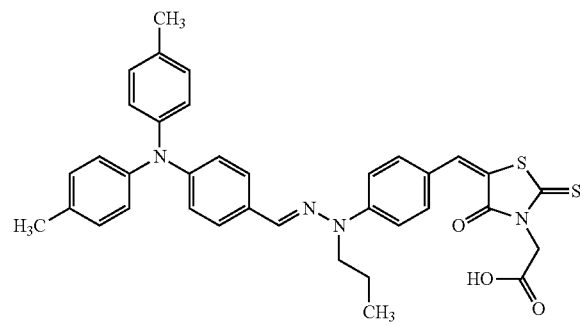 [SMILES: CCCN(/N=C/c1ccc(N(c2ccc(C)cc2)c2ccc(C)cc2)cc1)c1ccc(/C=C2/SC(=S)N(CC(=O)O)C2=O)cc1]

A mixture of D2-2 (0.165 g, 0.35 mmol), rhodanine-3-acetic acid (0.08 g, 0.11 mmol), and ammonium acetate (0.01 g, 0.11 mmol) was refluxed in acetic acid (0.6 mL) for 30 min. Afterwards, water (10 mL) was added and the extraction was done with ethyl acetate. The combined organic layer was washed with water, dried over anhydrous $Na_2SO_4$ and filtered. After evaporation of the solvent, the crude product was purified by column chromatography using 23:2 v/v toluene/methanol as an eluent to collect dye D2 as a dark red solid (0.18 g, 80%).

$^1$H NMR (300 MHz, $CDCl_3$, δ): 7.62-6.59 (m, 19H), 4.70 (s, 2H, $CH_2$), 3.62 (t, J=7.8 Hz, 2H, C$\underline{H}_2$CH$_2$CH$_3$), 2.30 (s, 6H, $CH_3$), 1.69-1.40 (m, 2H, $CH_2$C$\underline{H}_2$CH$_3$), 0.90 (t, J=7.3 Hz, 3H, $CH_2CH_2C\underline{H}_3$);

$^{13}$C NMR (75 MHz, $CDCl_3$, δ): 192.6, 170.0, 167.3, 148.46, 144.83, 143.59, 135.1, 134.12, 132.91, 129.91, 128.99, 128.18, 127.13, 125.94, 124.87, 121.74, 113.82, 47.1, 45.69, 21.2, 20.8, 18.10, 11.23;

IR (KBr): ν=3391 (OH), 3025 (aromatic CH); 2961, 2919, 2871 (aliphatic CH); 1705 (C=O); 1601, 1575, 1504 (C=C); 1293 (C=S); 1181, 1100 (C—N); 815 (CH=CH of 1,4-disubstituted benzenes);

Anal. calcd for $C_{36}H_{34}N_4O_3S_2$(%): C, 68.11; H, 5.40; N, 8.83. found: C, 68.00; H, 5.26; N, 8.61.

Preparation of Dye D3 a) 4-[Bis(9,9-dimethyl-9H-fluoren-2-yl)amino]benzaldehyde (D3-1; corresponds to compound 1 where both radicals R equal 9,9-dimethyl-9H-fluoren-2-yl)

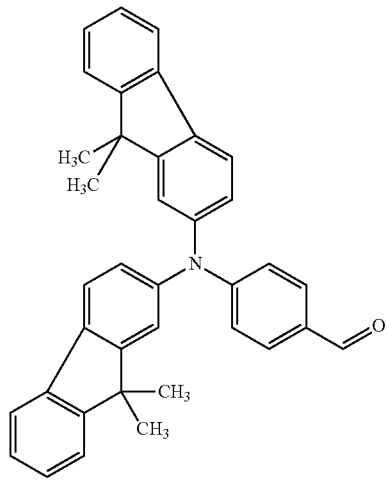 [SMILES: CC1(C)c2ccccc2-c2ccc(N(c3ccc(C=O)cc3)c3ccc4c(c3)C(C)(C)c3ccccc3-4)cc21]

Phosphorus oxychloride (1.30 mL, 14.13 mmol) was added portion-wise to DMF (1.1 mL, 14.13 mmol), not allowing the temperature of the mixture to rise above 5° C. N,N-bis(9,9-dimethylfluoren-2-yl)aniline (4.50 g, 9.42 mmol) was then added and the resulting mixture was heated at 90° C. for 4 h. The hot reaction mixture was poured into ice-water and neutralized by adding sodium acetate (3.47 g, 42.39 mmol) aqueous solution. After extraction with ethyl acetate and distilled water, the organic layer was dried over anhydrous Na$_2$SO$_4$, filtered, and solvent was evaporated. The crude product was purified by column chromatography using 3:22 v/v acetone/n-hexane as an eluent to collect compound D3-1 as a yellow solid (4.20 g, 88%).

$^1$H NMR (300 MHz, CDCl$_3$, δ): 9.83 (s, 1H, CHO), 7.76-7.60 (m, 6H), 7.43-7.11 (m, 12H), 1.42 (s, 12H, CH$_3$);

$^{13}$C NMR (75 MHz, CDCl$_3$, δ): 190.36, 155.37, 153.59, 145.58, 138.47, 136.11, 131.29, 129.21, 127.03, 124.78, 122.55, 120.90, 120.27, 119.96, 119.72, 46.90, 26.96;

Anal. calcd for C$_{37}$H$_{31}$NO (%): C, 87.89; H, 6.18; N, 2.77. found: C, 87.95; H, 6.27; N, 2.70.

b) 4-[Bis(9,9-dimethyl-9H-fluoren-2-yl)amino]benz-aldehyde-N-phenylhydrazone (D3-2; corresponds to compound 2 where both R equal 9,9-dimethyl-9H-fluoren-2-yl)

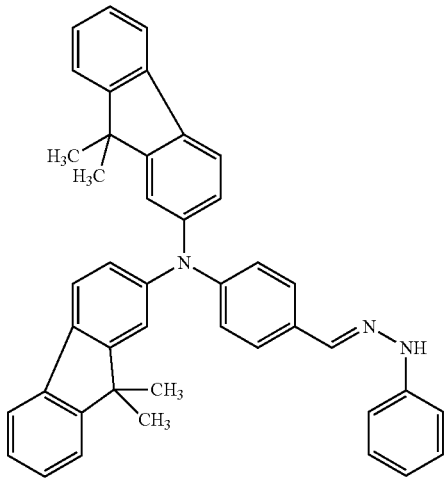 [SMILES: CC1(C)c2ccccc2-c2ccc(N(c3ccc(/C=N/Nc4ccccc4)cc3)c3ccc4c(c3)C(C)(C)c3ccccc3-4)cc21]

To compound D3-1 (3.50 g, 6.91 mmol) dissolved in a mixture of toluene (10 mL) and 2-propanol (2 mL), phenylhydrazine (1.00 mL, 10.16 mmol) was added. The mixture was refluxed until the arylaldehyde D3-1 disappeared (TLC, v/v acetone/n-hexane, 1:4). After reaction was complete solvents were removed under reduced pressure. Yellow crystals of 20 (3.58 g, 87%), formed upon adding the mixture of 2-propanol (15 mL) and toluene (4 mL), were filtered off and washed with 2-propanol. The crude product was used in the next step without additional purification.

c) 4-[Bis(9,9-dimethy-9H-fluoren-2-yl)amino]benz-aldehyde-N-(4-formylphenyl)-N-phenylhydrazone (D3-3; corresponds to compound 3 where both R equal 9,9-dimethyl-9H-fluoren-2-yl)

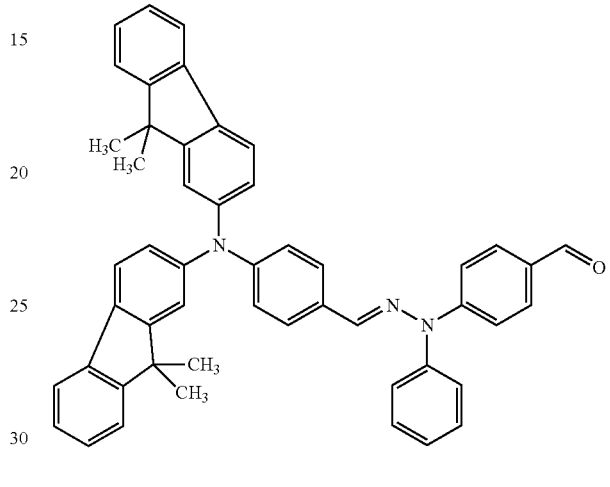

A mixture of compound D3-2 (3.19 g, 5.36 mmol), 4-fluorobenzaldehyde (1.73 mL, 16.10 mmol) and K$_2$CO$_3$ (4.45 g, 32.20 mmol) was refluxed in 25 mL anhydrous DMF under argon atmosphere for 16 h. After cooling to room temperature, 30 mL of distilled water were added and extraction was done with ethyl acetate. The organic layer was washed with water, dried over anhydrous Na$_2$SO$_4$ and filtered. After evaporation of the solvent, the crude product was purified by column chromatography using 10:1:14 v/v toluene/ethyl acetate/n-hexane as an eluent to collect compound D3-3 as a yellow solid (2.10 g, 56%).

$^1$H NMR (300 MHz, CDCl$_3$, δ): 9.81 (s, 1H, CHO), 7.73 (d, J=9.0 Hz, 2H), 7.68-7.49 (m, 8H), 7.41-7.13 (m, 18H), 7.11 (d, J=2.0 Hz, 1H), 7.08 (d, J=2.0 Hz, 1H), 1.40 (s, 12H, CH$_3$);

$^{13}$C NMR (75 MHz, CDCl$_3$, δ): 190.68, 155.08, 153.47, 151.99, 148.83, 146.76, 138.86, 138.78, 138.36, 134.61, 131.36, 131.09, 129.85, 129.41, 128.85, 128.69, 127.72, 126.99, 126.60, 123.50, 123.03, 122.47, 120.63, 119.45, 118.96, 114.04, 46.81, 27.00;

IR (KBr): ν=3035 (aromatic CH); 2956, 2921, 2858, 2725 (aliphatic CH); 1689 (CHO); 1598, 1588, 1564, 1505, 1487 (C=C); 1157, 1117 (C—N); 867, 826 (CH=CH of 1,4-disubstituted benzene); 778, 758, 736 (CH=CH of mono-substituted benzene).

Anal. calcd for C$_{50}$H$_{41}$N$_3$O (%): C, 85.81; H, 5.90; N, 6.00. found: C, 85.70; H, 5.94; N, 6.03.

d) 4-[Bis(9,9-dimethyl-9H-fluoren-2-yl)amino]benzaldehyde-N-4-(3-carboxymethyl-4-oxo-2-thioxo-1,3-thiazolidin-5-ylidenmethyl)phenyl-N-phenylhydrazone (D3)

Preparation of Dye D4 a) 4-[Bis(9,9-dimethyl-9H-fluoren-2-yl)amino]benzaldehyde-N-phenyl-N-propylhydrazone (D4-1; corresponds to compound 4 where both radicals R equal 9,9-dimethyl-9H-fluoren-2-yl)

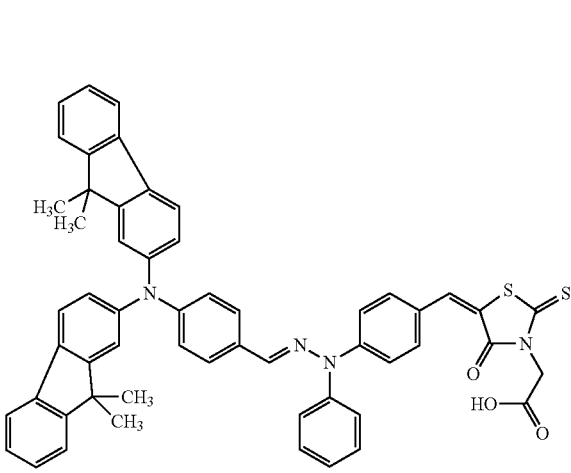 [SMILES: CC1(C)c2ccccc2-c2ccc(N(c3ccc(/C=N/N(c4ccccc4)c4ccc(/C=C5/SC(=S)N(CC(=O)O)C5=O)cc4)cc3)c3ccc4c(c3)C(C)(C)c3ccccc3-4)cc21]

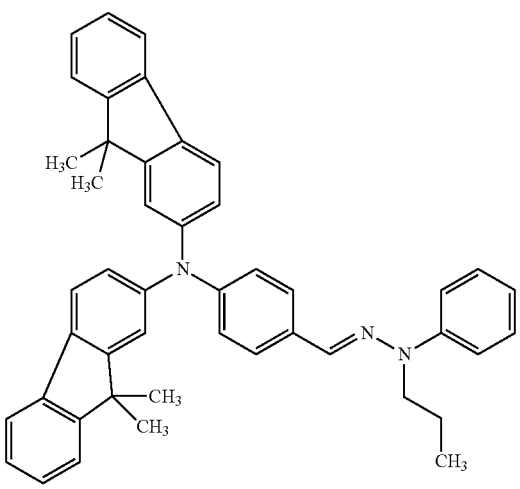 [SMILES: CCCN(/N=C/c1ccc(N(c2ccc3c(c2)C(C)(C)c2ccccc2-3)c2ccc3c(c2)C(C)(C)c2ccccc2-3)cc1)c1ccccc1]

A mixture of compound D3-3 (0.70 g, 1.00 mmol), rhodanine-3-acetic acid (0.23 g, 1.2 mmol), and ammonium acetate (0.02 g, 0.29 mmol) was refluxed in acetic acid (7 mL) for 3.5 h. Afterwards, 20 mL of water was added and the extraction was done with ethyl acetate. The organic layer was washed with distilled water, dried over anhydrous $Na_2SO_4$ and filtered. After evaporation of the solvent, the crude product was purified by column chromatography using toluene followed by 23:2 v/v toluene/methanol as an eluent to collect dye D3 as a dark red solid (0.58 g, 67%).

$^1$H NMR (300 MHz, $CDCl_3$, δ): 7.96-6.85 (m, 30H), 4.90 (s, 2H, $CH_2$), 1.46 (s, 12H, $CH_3$);

$^{13}$C NMR (75 MHz, $CDCl_3$, δ): 192.61, 171.46, 167.44, 155.34, 155.08, 153.59, 153.47, 146.70, 145.56, 138.79, 138.51, 134.55, 132.66, 131.04, 129.71, 129.34, 128.99, 128.18, 127.71, 126.99, 126.60, 125.27, 124.58, 123.50, 123.02, 122.47, 120.89, 120.64, 120.04, 119.71, 119.45, 118.96, 114.96, 46.88, 46.80, 26.99;

IR (KBr): ν=3545 (OH); 3034 (aromatic CH); 2956, 2920, 2858 (aliphatic CH); 1710 (C=O); 1574, 1504, 1488 (C=C); 1297 (C=S); 1198, 1175, 1135, 1104 (C—N); 868, 824 (CH=CH of 1,4-disubstituted benzene); 777, 757, 735 (CH=CH of monosubstituted benzene);

Anal. calcd. for $C_{55}H_{44}N_4O_3S_2$(%): C, 75.66; H, 5.08; N, 6.42. found: C, 75.74; H, 5.16; N, 6.32.

To a refluxing mixture of compound 2 (3.05 g, 5.11 mmol; both radicals R equal 9,9-dimethyl-9H-fluoren-2-yl), 1-bromopropane (2.77 mL, 30.66 mmol) in anhydrous THF (5 mL), powdered KOH (1.06 g, 18.89 mmol) and anhydrous $Na_2SO_4$ (0.40 g, 2.81 mmol) were added in three equal portions every 1 h. After 3.5 hours the reaction mixture was extracted with ethyl acetate and distilled water until neutral. The organic layer was dried over anhydrous $Na_2SO_4$, filtered off and ethyl acetate was removed. The crude product was purified by column chromatography using 3:22 v/v acetone/n-hexane as an eluent to collect compound D4-1 as a yellow solid (3.01 g, 92%).

$^1$H NMR (300 MHz, $CDCl_3$, δ): 7.68-7.55 (m, 6H), 7.51 (s, 1H), 7.42-7.05 (m, 16H), 6.89 (t, J=6.9 Hz, 1H), 3.86 (t, J=7.7 Hz, 2H, $CH_2CH_2CH_3$), 1.79-1.65 (m, 2H, $CH_2C\underline{H}_2CH_3$), 1.41 (s, 12H, $CH_3$), 1.03 (t, J=7.3 Hz, 3H, $CH_2CH_2C\underline{H}_3$);

$^{13}$C NMR (75 MHz, $CDCl_3$, δ): 155.02, 153.49, 147.51, 147.15, 138.93, 134.16, 131.20, 130.86, 129.03, 126.96, 126.86, 126.45, 123.84, 123.17, 122.45, 120.57, 120.02, 119.38, 118.59, 114.54, 46.88, 46.81, 27.02, 18.31, 11.37;

Anal. calcd for $C_{46}H_{43}N_3$(%): C, 86.62; H, 6.79; N, 6.59. found: C, 86.70; H, 6.69; N, 6.61.

b) 4-[Bis(9,9-dimethyl-9H-fluoren-2-yl)amino]benz-aldehyde-N-4-formylphenyl-N-propylhydrazone (D4-2)

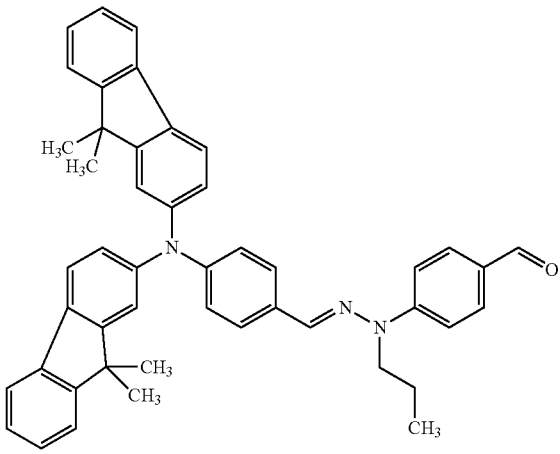 [SMILES: CCCN(/N=C/c1ccc(N(c2ccc3c(c2)C(C)(C)c2ccccc2-3)c2ccc3c(c2)C(C)(C)c2ccccc2-3)cc1)c1ccc(C=O)cc1]

Phosphorus oxychloride (1.06 mL, 11.60 mmol) was added drop wise to DMF (5.70 mL, 74.07 mmol) not allowing the temperature of the mixture to rise above 5° C. A solution of 22 (5.00 g, 7.84 mmol) in DMF (14.5 mL) was then added and the resulting mixture was heated at 60° C. for 50 min. The hot reaction mixture was poured into ice-water, neutralized by adding sodium acetate (2.85 g, 34.80 mmol) aqueous solution, and extracted with ethyl acetate. The organic layer was dried over anhydrous $Na_2SO_4$, filtered, and solvent was evaporated. Crude product was purified by column chromatography using 3:22 v/v acetone/hexane as an eluent to collect compound D4-2 as a yellow solid (1.16 g, 22%).

$^1$H NMR (300 MHz, $CDCl_3$, δ): 9.87 (s, 1H, CHO), 7.85 (d, J=8.9 Hz, 2H), 7.74-7.63 (m, 7H), 7.52-7.22 (m, 12H), 7.18 (d, J=2.0 Hz, 1H), 7.15 (d, J=2.0 Hz, 1H), 3.96 (t, J=7.8 Hz, 2H, $CH_2CH_2CH_3$), 1.87-1.72 (m, 2H, $CH_2CH_2CH_3$), 1.47 (s, 12H, $CH_3$), 1.12 (t, J=7.3 Hz, 3H, $CH_2CH_2CH_3$);

$^{13}$C NMR (75 MHz, $CDCl_3$, δ): 190.61, 155.13, 153.52, 151.57, 148.64, 146.86, 138.83, 134.78, 134.60, 131.62, 129.56, 128.39, 127.55, 127.00, 126.60, 123.51, 123.22, 122.49, 120.64, 119.46, 118.96, 113.41, 46.84, 46.08, 27.02, 18.51, 11.28; IR (KBr): ν=3747, 3186, 3035, 3010 (aromatic CH); 2957, 2921, 2858, 2724 (aliphatic CH); 1676 (CHO); 1595, 1565, 1505, 1486 (C=C); 1163, 1109 (C—N); 826 (CH=CH of 1,4-disubstituted benzene);

Anal. calcd. for $C_{47}H_{43}N_3O$ (%): C, 84.78; H, 6.51; N, 6.31. found: C, 84.82; H, 6.59; N, 6.41.

c) 4-[Bis(9,9-dimethyl-9H-fluoren-2-yl)amino]benz-aldehyde-N-4-(3-carboxymethyl-4-oxo-2-thioxo-1,3-thiazolidin-5-ylidenmethyl)phenyl-N-propylhydrazone (D4)

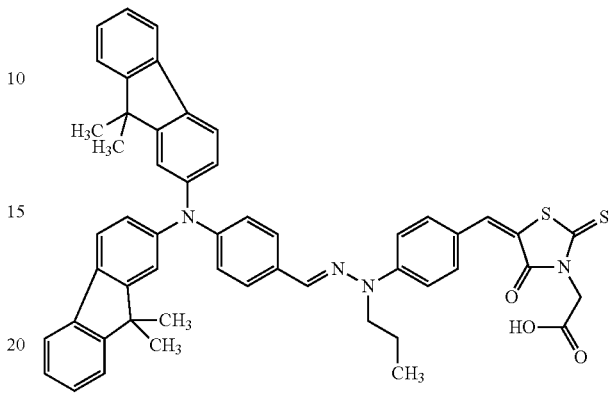

A mixture of 23 (0.58 g, 0.88 mmol) and rhodanine-3-acetic acid (0.20 g, 1.05 mmol) was refluxed in acetic acid (3.0 mL) for 2 h. Afterwards, water (15 mL) was added and the extraction was done with ethyl acetate. The organic layer was washed with distilled water, dried over anhydrous $Na_2SO_4$, filtered, and solvent evaporated. The crude product was purified by column chromatography using toluene followed by 23:2 v/v toluene/methanol as an eluent to collect dye D4 as a dark red solid (0.43 g, 58%).

$^1$H NMR (300 MHz, $CDCl_3$, δ): 7.74-7.52 (m, 6H), 7.47-7.03 (m, 19H), 4.87 (s, 2H, $CH_2$), 3.87 (t, J=7.8 Hz, 2H, $CH_2CH_2CH_3$), 1.78-1.65 (m, 2H, $CH_2CH_2CH_3$), 1.41 (s, 12H, $CH_3$), 1.04 (t, J=7.3 Hz, 3H, $CH_2CH_2CH_3$);

$^{13}$C NMR (75 MHz, $CDCl_3$, δ): 192.58, 171.04, 167.31, 155.36, 155.08, 153.58, 146.82, 145.51, 138.81, 138.47, 136.02, 134.56, 132.89, 132.51, 128.98, 128.17, 126.99, 125.24, 124.60, 123.48, 122.53, 120.89, 120.64, 120.07, 119.71, 119.44, 118.93, 114.18, 46.89, 46.80, 44.65, 27.00, 18.49, 11.29;

IR (KBr): ν=3635 (OH); 3032 (aromatic CH); 2957, 2921, 2859 (aliphatic CH); 1709 (C=O); 1602, 1573, 1505, 1486 (C=C); 1298 (C=S); 1182, 1100 (C—N); 823 (CH=CH of 1,4-disubstituted benzene);

Anal. calcd. for $C_{52}H_{46}N_4O_3S_2$(%): C, 74.43; H, 5.53; N, 6.68. found: C, 74.55; H, 5.61; N, 6.59.

Preparation of Dye D5 a)
4-(diphenylamino)benzaldehyde-N-phenylhydrazone
(D5-1; corresponds to compound 2 where both radicals R equal phenyl)

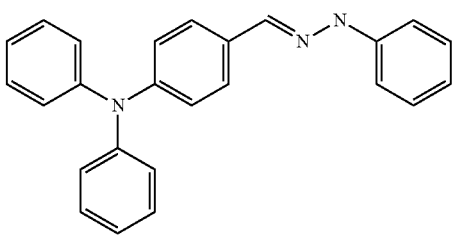 [SMILES: C(=N\Nc1ccccc1)/c1ccc(N(c2ccccc2)c2ccccc2)cc1]

Compound D5-1 was prepared according to Urnikaite S., Daskeviciene M., Malinauskas T., Jankauskas V., Getautis V., Monast. Chem., 2009, 140(12), 2005-2007.

b) 4-(diphenylamino)benzaldehyde-N-(4-formyl)phenyl-N-phenylhydrazone (D5-2; corresponds to compound 3 where both radicals R equal phenyl)

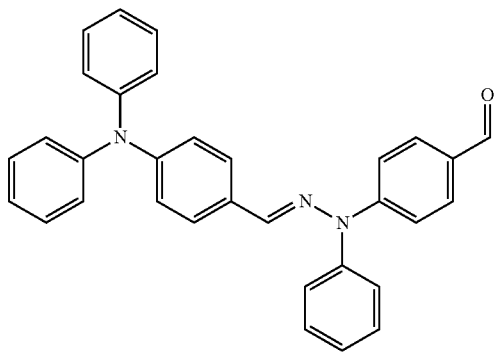 [SMILES: O=Cc1ccc(N(/N=C/c2ccc(N(c3ccccc3)c3ccccc3)cc2)c2ccccc2)cc1]

A mixture of 1 (3.00 g, 8.25 mmol), 4-fluorobenzaldehyde (2.66 ml, 24.76 mmol) and $K_2CO_3$ (6.80 g, 49.52 mmol) was refluxed in 25 mL anhydrous DMF under argon atmosphere for 15 h. After cooling to room temperature, 30 mL of distilled water were added and extraction was done with ethyl acetate. The organic layer was washed with distilled water, dried over anhydrous sodium sulfate and filtered. After evaporation of the solvent, the crude product was purified by column chromatography using 10:1:14 v/v toluene/ethyl acetate/hexane as an eluent to collect compound D5-2 as a yellow solid (1.98 g, 52%).

$^1$H NMR (300 MHz, CDCl$_3$, δ): 9.80 (s, 1H), 7.72 (d, J=8.9 Hz, 2H), 7.68-7.58 (m, 2H), 7.57-7.43 (m, 3H), 7.30-6.97 (m, 17H);

$^{13}$C NMR (75 MHz, CDCl$_3$, δ): 190.68, 151.97, 148.65, 147.16, 138.80, 138.29, 131.33, 131.06, 129.81, 129.30, 128.97, 128.74, 128.61, 127.65, 124.76, 123.38, 122.69, 113.98;

IR (KBr): ν (cm$^{-1}$)=3058, 3033 (aromatic CH); 2802, 2727, 2623 (aliphatic CH); 1688 (CHO); 1588, 1563, 1505, 1487 (C=C); 1157, 1117 (C—N); 863, 826 (CH=CH of 1,4-disubstituted benzenes), 753, 738 (CH=CH of monosubstituted benzenes);

Anal. calcd. for $C_{32}H_{25}N_3O$ (%): C, 82.20; H, 5.39; N, 8.99. found: C, 82.11; H, 5.41; N, 9.03.

c) 4-(diphenylamino)benzaldehyde-N-4-(3-carboxymethyl-4-oxo-2-thioxo-1,3-thiazolidin-5-ylidenmethyl)phenyl-N-phenylhydrazone (D5)

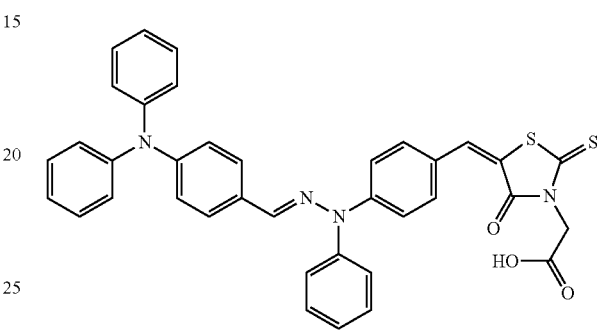

A mixture of compound D5-2 (0.31 g, 0.67 mmol), rhodanine-3-acetic acid (0.15 g, 0.80 mmol) and ammonium acetate (0.015 g, 0.20 mmol) was refluxed in acetic acid (4.0 mL) for 4.5 h. Afterwards, 10 mL of water were added and the extraction was done with chloroform. The organic layer was washed with distilled water, dried over anhydrous $Na_2SO_4$ and filtered. After evaporation of the solvent, the crude product was purified by column chromatography using 10:1:14 v/v toluene/ethyl acetate/hexane followed by 23:2 v/v toluene/methanol as an eluent to collect dye D5 as a dark red solid (0.28 g, 67%).

$^1$H NMR (300 MHz, 50% DMSO-d$_6$/CDCl$_3$, δ): 7.82-6.64 (m, 25H), 4.63 (s, 2H);

$^{13}$C NMR (75 MHz, 50% DMSO-d$_6$/CDCl$_3$, δ): 191.02, 165.29, 147.28, 146.59, 145.22, 144.14, 136.20, 131.63, 131.05, 130.68, 129.48, 128.04, 127.72, 127.22, 126.96, 126.46, 126.03, 124.26, 122.95, 121.82, 120.65, 113.15, 44.93;

IR (KBr): ν (cm$^{-1}$)=3614 (OH); 3032 (aromatic CH), 2924 (aliphatic CH); 1709 (C=O); 1575, 1504 (C=C); 1294 (C=S); 1198, 1175, 1135, 1104 (C—N); 823 (CH=CH of 1,4-disubstituted benzenes); 752, 723 (CH=CH of monosubstituted benzenes);

Anal. calcd. for $C_{37}H_{28}N_4O_3S_2$(%): C, 69.35; H, 4.40; N, 8.74. found: C, 69.28; H, 4.42; N, 8.77.

Preparation of Dye D6 a) 4-(4,4'-dimethyldiphenylamino)benzaldehyde-N-phenylhydrazone (D6-1; corresponds to compound 2 where both radicals R equal 4-methylphenyl)

b) 4-(4,4'-dimethyldiphenylamino)benzaldehyde-N-(4-formylphenyl)-N-phenylhydrazone (D6-3; corresponds to compound 3 where both radicals R equal 4-methylphenyl)

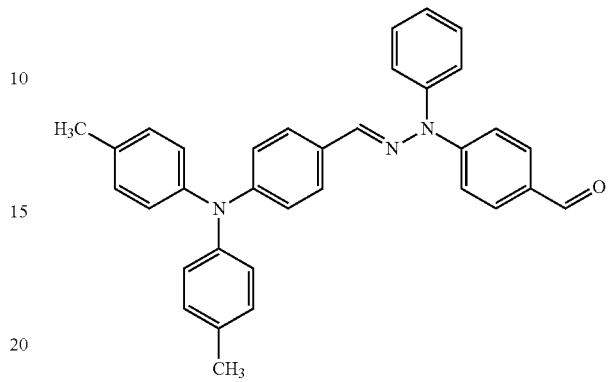

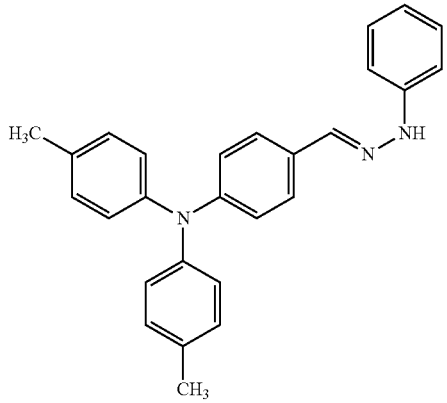 [SMILES: Cc1ccc(N(c2ccc(C)cc2)c2ccc(/C=N/Nc3ccccc3)cc2)cc1]

A mixture of D6-2 (3.27 g, 8.35 mmol), 4-fluorobenzaldehyde (2.69 ml, 25.07 mmol), and $K_2CO_3$ (6.93 g, 50.14 mmol) were refluxed in anhydrous DMF (25 mL) under argon atmosphere for 24 h. After cooling to room temperature, distilled water (30 mL) was added and mixture was extracted with ethyl acetate, dried over anhydrous $Na_2SO_4$, filtered and solvent was evaporated. The crude product was purified by column chromatography using 10:1:14 v/v toluene/ethyl acetate/n-hexane as an eluent to collect compound D6-3 as a yellow solid (2.76 g, 67%).

$^1$H NMR (300 MHz, CDCl$_3$, δ): 9.80 (s, 1H, CHO), 7.72 (d, J=8.9 Hz, 2H), 7.67-7.49 (m, 2H), 7.44 (d, J=8.8 Hz, 2H), 7.27-6.93 (m, 16H), 2.31 (s, 6H, CH$_3$);

$^{13}$C NMR (75 MHz, CDCl$_3$, δ): 190.70, 152.04, 149.09, 144.65, 139.11, 138.35, 133.14, 131.97, 131.35, 131.04, 129.93, 129.84, 129.33, 127.57, 125.02, 121.42, 115.03, 113.93, 20.81;

IR (KBr): ν=3347, 3071, 3054 (aromatic CH); 2951, 2850, 2817, 2764 (aliphatic CH); 1685 (CHO); 1603, 1678, 1505, 1465 (C=C); 1169, 1157, 1112 (C—N); 875, 822 (CH=CH of 1,4-disubstituted benzenes), 796, 735 (CH=CH of monosubstituted benzene);

Anal. calcd for $C_{34}H_{29}N_3O$ (%): C, 82.40; H, 5.90; N, 8.48. found: C, 82.31; H, 5.95; N, 8.53.

To compound 1 (3.50 g, 6.91 mmol; both radicals R equal 4-methylphenyl) dissolved in toluene (10 mL) and 2-propanol (2 mL), phenylhydrazine (1.00 mL, 10.16 mmol) was added. The mixture was refluxed until the compound 1 disappeared (TLC, acetone: n-hexane=1:4). At the end of the reaction, the mixture was cooled to room temperature. Yellow crystals, having formed upon standing, were filtered off and washed with a mixture of 2-propanol and n-hexane (1:1) to give the corresponding compound D6-2 (4.03, 89%), which was used in the next reaction without further purification.

c) 4-(4,4'-dimethyldiphenylamino)benzaldehyde-N-4-[3-(4-carboxy)phenyl-4-oxo-2-thioxo-1,3-thiazolidin-5-ylidenmethyl]phenyl-N-phenylhydrazone (D6)

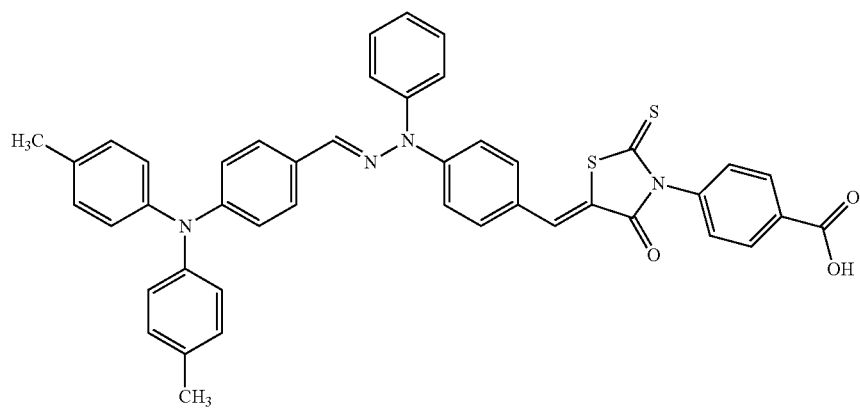 [SMILES: Cc1ccc(N(c2ccc(C)cc2)c2ccc(/C=N/N(c3ccccc3)c3ccc(/C=C4\SC(=S)N(c5ccc(C(=O)O)cc5)C4=O)cc3)cc2)cc1]

A mixture of D6-3 (0.30 g, 0.61 mmol), 4-(4-oxo-2-thioxo-1,3-thiazolidin-3-yl)benzoic acid (0.18 g, 0.73 mmol) and ammonium acetate (0.017 g, 0.22 mmol) was refluxed in acetic acid (3.0 mL) for 6 h. At the end of the reaction, the mixture was cooled to room temperature. The crystals formed upon standing were filtered off and washed with 2-propanol. The crude product was purified by column chromatography using 2:23 v/v methanol/toluene as an eluent to collect dye D6 as a dark red solid (0.196 g, 72%).

$^1$H NMR (300 MHz, CDCl$_3$, δ): 8.25 (d, J=8.4 Hz, 2H), 7.76-6.91 (m, 25H), 2.34 and 2.31 (two s of isomeric CH$_3$, 6H);

$^{13}$C NMR (75 MHz, CDCl$_3$, δ): 192.86, 170.61, 167.49, 149.54, 149.17, 144.67, 139.81, 139.20, 138.25, 134.78, 133.20, 132.68, 131.32, 131.07, 130.34, 129.96, 129.36, 128.83, 127.63, 126.20, 125.07, 121.43, 119.15, 117.45, 114.87, 20.94, 20.83;

IR (KBr): ν=3431 (OH); 3025 (aromatic CH); 2918, 2857 (aliphatic CH); 1698 (C=O); 1661, 1574, 1504, (C=C); 1294 (C=S); 1173, 1150 (C—N); 858, 815, 796 (CH=CH of 1,4-disubstituted benzenes); 754, 728, 716, 697 (CH=CH of monosubstituted benzene);

Anal. calcd for C$_{44}$H$_{34}$N$_4$O$_3$S$_2$(%): C, 72.31; H, 4.69; N, 7.67. found: C, 72.36; H, 4.70; N, 7.63.

Preparation of Dye D7 a) 4-(4-methyldiphenylamino)benzaldehyde-N-phenylhydrazone (D7-1; corresponds to compound 2 where one radical R equals phenyl and the other radical R 4-methylphenyl)

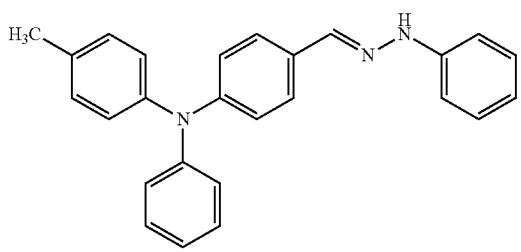 [SMILES: Cc1ccc(N(c2ccccc2)c2ccc(/C=N/Nc3ccccc3)cc2)cc1]

To 4-[(4-methyldiphenyl)amino]benzaldehyde (6 g, 20.88 mmol) dissolved in toluene (30 mL) and 2-propanol (5 mL), phenylhydrazine (3.00 mL, 31.32 mmol) was added. The mixture was refluxed until the arylaldehyde disappeared (TLC, acetone:n-hexane=3:22). At the end of the reaction, the mixture was cooled to room temperature. Yellow crystals, having formed upon standing, were filtered off and washed with a mixture of 2-propanol and n-hexane (1:1) to give the corresponding phenylhydrazone D7-1 (6.26, 80%), which was used in the next reaction without further purification.

b) 4-(4-methyldiphenylamino)benzaldehyde-N-(4-formyl)phenyl-N-phenylhydrazone (D7-2)

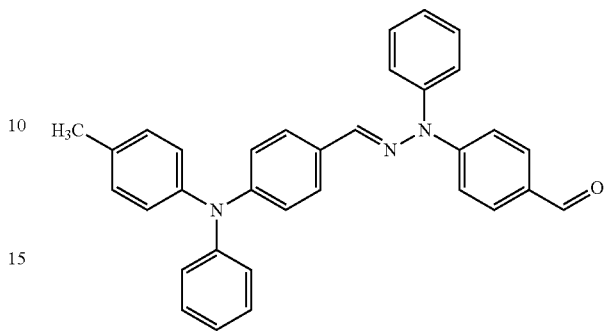

A mixture of compound D7-1 (2.65 g, 7.02 mmol), 4-fluorobenzaldehyde (1.63 mL, 15.19 mmol) and K$_2$CO$_3$ (4.0 g, 28.94 mmol) was refluxed in 20 mL anhydrous DMF under argon atmosphere for 12 h. After cooling to room temperature, 40 mL of distilled water were added and extraction was done with ethyl acetate. The organic layer was washed with water, dried over anhydrous Na$_2$SO$_4$ and filtered. After evaporation of the solvent, the crude product was purified by column chromatography using 1:24 v/v acetone/n-hexane as an eluent to collect compound D7-2 as a yellow solid (2.35 g, 70%).

$^1$H NMR (300 MHz, CDCl$_3$, δ): 9.80 (s, 1H, CHO), 7.72 (d, J=8.9 Hz, 2H), 7.68-7.49 (m, 3H), 7.46 (d, J=8.7 Hz, 2H), 7.29-6.93 (m, 16H), 2.31 (s, 3H);

$^{13}$C NMR (75 MHz, CDCl$_3$, δ): 190.65, 152.02, 148.87, 147.29, 144.56, 138.97, 138.37, 133.46, 131.33, 131.05, 130.01, 129.83, 129.35, 129.22, 128.60, 128.30, 127.62, 125.37, 124.39, 123.06, 122.10, 113.09, 20.84;

IR (KBr): ν=3034 (aromatic CH); 2921, 2804, 2728, 2627 (aliphatic CH); 1688 (C=O); 1599, 1588, 1562, 1505, 1489 (C=C); 1157, 1116, 1097 (C—N); 824, 797 (CH=CH of 1,4-disubstituted benzenes); 754, 735, 725, 698 (CH=CH of monosubstituted benzenes);

Anal. calcd for C$_{33}$H$_{27}$N$_3$O (%): C, 82.30; H, 5.65; N, 8.73. found: C, 82.33; H, 5.71; N, 8.83.

c) 4-(4-methyldiphenylamino)benzaldehyde-N-4-(3-carboxymethyl-4-oxo-2-thioxo-1,3-thiazolidin-5-ylidenmethyl)phenyl-N-phenylhydrazone (D7)

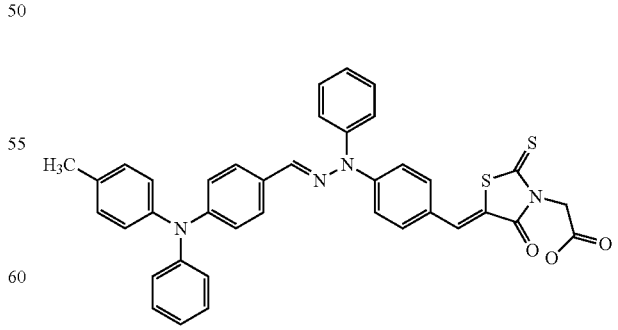

A mixture of D7-2 (1.20 g, 2.49 mmol), rhodanine-3-acetic acid (0.57 g, 2.99 mmol), and ammonium acetate (0.06 g, 0.75 mmol) was refluxed in acetic acid (15 mL) for 3.5 h. Afterwards, water (40 mL) was added and the extraction was done with ethyl acetate. The organic layer was washed with water, dried over anhydrous Na$_2$SO$_4$ and filtered. After evaporation of the solvent, the crude product was purified by column chromatography using 23:2 v/v toluene/methanol as an eluent to collect dye D7 as a dark red solid (0.45 g, 28%).

$^1$H NMR (300 MHz, 50% DMSO-d$_6$/CDCl$_3$, δ): 7.84-6.74 (m, 24H), 4.62 (s, 2H), 2.32 and 2.29 (two s of isomeric CH$_3$, 3H);

IR (KBr): ν=3481 (OH); 3026 (aromatic CH); 2920, 2853, 2604 (aliphatic CH); 1706 (C=O); 1591, 1577, 1504, 1491 (C=C); 1293 (C=S); 1175, 1136, 1105 (C—N); 863, 824, 779 (CH=CH of 1,4-disubstituted benzenes); 750, 696 (CH=CH of monosubstituted benzenes);

Anal. calcd for C$_{38}$H$_{30}$N$_4$O$_3$S$_2$(%): C, 69.70; H, 4.62; N, 8.56. found: C, 69.68; H, 4.60; N, 8.66.

A2) Preparation of Dyes D8 and D9

Similar to the preparation of dyes D1 to D7, condensation of dialdehydes with the corresponding hydrazine derivatives yielded dihydrazones, which were used in arylation (with 4-fluorobenzaldehyde) or alkylation (with 1-bromononane) reactions and the resulting alkylated intermediate was subjected to a Vilsmeier-Haack reaction and the mono-formylated dihydrazone was isolated. Finally, condensation of the obtained aldehydes with rhodanine-3-acetic acid yielded dyes ID-1370 (D8) and ID-1492 (D9).

The detailed synthetic procedures are as follows:

Preparation of Dye D8 a) 4-(4-formyl-4'-methyldiphenylamino)benzaldehyde (D8-1)

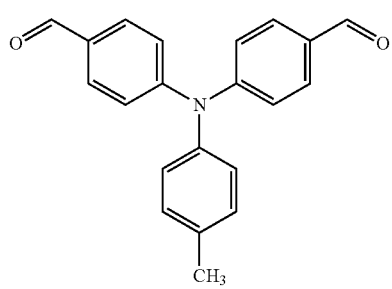 [SMILES: Cc1ccc(N(c2ccc(C=O)cc2)c2ccc(C=O)cc2)cc1]

Compound D8-1 was prepared according to Getautis V., Daskeviciene M., Malinauskas T., Stanisauskaite A., Stumbraite J., Molecules 2006, 11, 64-71.

b) 4-(4-formyl-4'-methyldiphenylamino)benzaldehyde bis(N-phenylhydrazone) (D8-2)

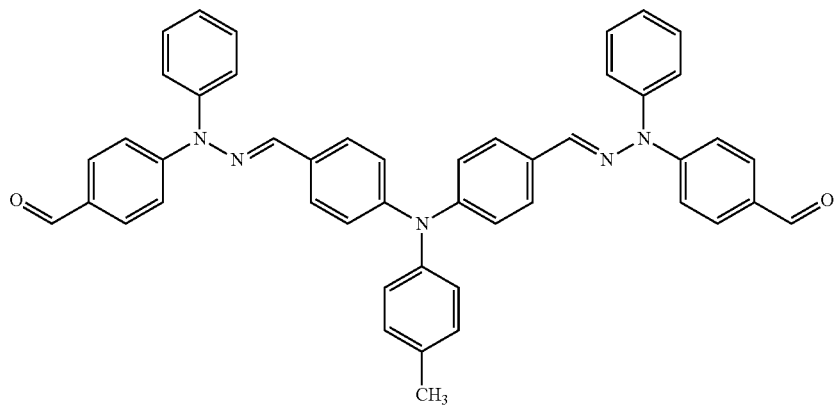 [SMILES: Cc1ccc(N(c2ccc(/C=N/N(c3ccccc3)c3ccc(C=O)cc3)cc2)c2ccc(/C=N/N(c3ccccc3)c3ccc(C=O)cc3)cc2)cc1]

To compound D8-1 (2.76 g, 8.75 mmol), dissolved in tetrahydrofuran (8 mL) and 2-propanol (22 mL), phenylhydrazine (2.15 mL, 21.88 mmol) was added. The mixture was refluxed until the aldehyde disappeared. After completion of the reaction, the mixture was cooled to room temperature and crystals having formed upon standing were filtered off and washed with 2-propanol to give compound D8-2 (4.03 g, 93%), which was used in the next step without further purification.

b) 4-(4-formyl-4'-methyldiphenylamino)benzaldehyde bis[N-(4-formyl)phenyl-N-phenylhydrazone] (D8-3)

A mixture of D8-2 (2.80 g, 5.65 mmol), 4-fluorobenzaldehyde (1.82 mL, 16.95 mmol) and $K_2CO_3$ (4.68 g, 33.89 mmol) was refluxed in 21 mL anhydrous DMF under argon atmosphere for 20 h. After cooling to room temperature, 30 mL of distilled water were added and extraction was done with ethyl acetate. The organic layer was washed with water, dried over anhydrous $Na_2SO_4$ and filtered. After evaporation of the solvent, the crude product was purified by column chromatography using 3:3:19 v/v acetone/diethyl ether/n-hexane as an eluent to collect 13 as a yellow solid (1.39 g, 35%).

$^1$H NMR (300 MHz, $CDCl_3$, δ): 9.80 (s, 2H), 7.78-7.38 (m, 14H), 7.30-6.93 (m, 18H);

$^{13}$C NMR (75 MHz, $CDCl_3$, δ): 151.94, 148.13, 144.06, 138.63, 138.27, 134.06, 131.33, 131.08, 130.14, 129.79, 129.41, 129.22, 128.68, 127.68, 125.66, 123.10, 114.03, 20.87;

Anal. calcd for $C_{47}H_{37}N_5O_2$(%): C, 80.21; H, 5.30; N, 9.95. found: C, 80.19; H, 5.43; N, 9.92.

c) 4-(4-formyl-4'-methyldiphenylamino)benzaldehyde bis[N-4-(3-carboxymethyl-4-oxo-2-thioxo-1,3-thiazolidin-5-ylidenmethyl)phenyl-N-phenylhydrazone] (D8)

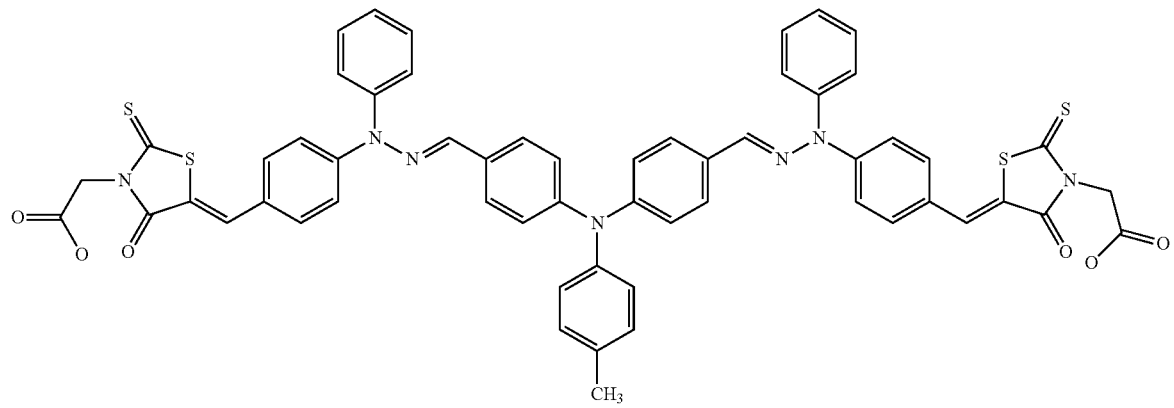 [SMILES: Cc1ccc(N(c2ccc(/C=N/N(c3ccccc3)c3ccc(/C=C4\SC(=S)N(CC(=O)O)C4=O)cc3)cc2)c2ccc(/C=N/N(c3ccccc3)c3ccc(/C=C4\SC(=S)N(CC(=O)O)C4=O)cc3)cc2)cc1]

A mixture of D8-3 (0.95 g, 1.35 mmol), rhodanine-3-acetic acid (0.62 g, 2.19 mmol) and ammonium acetate (0.06 g, 0.81 mmol) was refluxed in acetic acid (20 mL) for 22 h. Afterwards, water (30 mL) was added and the extraction was done with toluene. The organic layer was dried over anhydrous $Na_2SO_4$, filtered, and solvent evaporated. The crude product was purified by column chromatography using 7:18 v/v acetone/n-hexane followed by 3:22 v/v toluene/methanol as an eluent to collect dye D8 as a dark red solid (0.26 g, 19%).

$^1$H NMR (300 MHz, 50% DMSO-$d_6$/$CDCl_3$): •=8.13-6.72 (m, 34H), 4.70 (s, 4H), 2.31 (s, 3H);

Anal. calcd for $C_{57}H_{43}N_7O_6S_4$(%): C, 65.19; H, 4.13; N, 9.34. found: C, 65.11; H, 4.15; N, 9.33.

Preparation of Dye D9 a) 4-(4-formyldiphenylamino)benzaldehyde bis(N-phenylhydrazone) (D9-1)

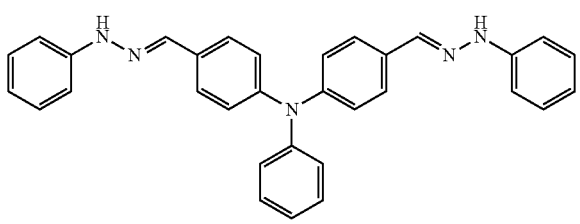 [SMILES: C(=N\Nc1ccccc1)/c1ccc(N(c2ccccc2)c2ccc(/C=N/Nc3ccccc3)cc2)cc1]

To D8-1 (11.55 g, 38.32 mmol), dissolved in toluene (50 mL), phenylhydrazine (9.0 mL, 91.97 mmol) was added. The mixture was refluxed until the aldehyde disappeared (TLC, acetone:n-hexane=7:18). At the end of the reaction, the mixture was cooled to room temperature. The crystals having formed upon standing were filtered off and washed with 2-propanol to give compound D9-1 (15.0 g, 82%), which was used in the next reaction without further purification.

b) 4-(4-formyldiphenylamino)benzaldehyde bis(N-nonyl-N-phenylhydrazone) (D9-2)

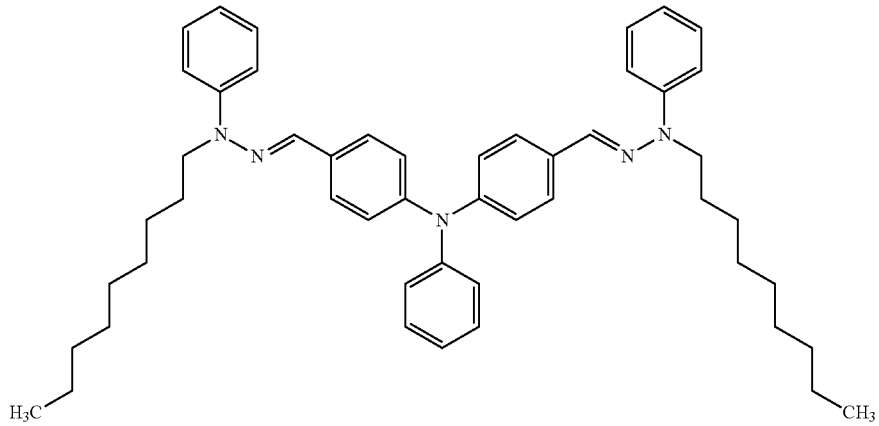 [SMILES: CCCCCCCCCN(/N=C/c1ccc(N(c2ccccc2)c2ccc(/C=N/N(CCCCCCCCC)c3ccccc3)cc2)cc1)c1ccccc1]

To a refluxing mixture of compound D9-1 (5.0 g, 10.38 mmol), 1-bromononane (15.0 mL, 78.78 mmol) in anhydrous THF (30 mL), powdered KOH (1.92 g, 34.22 mmol) and anhydrous $Na_2SO_4$ (0.60 g, 4.22 mmol) were added in three equal portions every 1 h. After 19 hours the reaction mixture was extracted with ethyl acetate and distilled water until neutral. The organic layer was dried over anhydrous $Na_2SO_4$, filtered off and ethyl acetate was removed. The crude product was purified by column chromatography using n-hexane to collect unreacted 1-bromononane, followed by 3:22 v/v toluene/n-hexane as an eluent to collect compound D9-2 as a yellow solid (6.72 g, 88%).

$^1$H NMR (300 MHz, $CDCl_3$, δ): 7.58 (d, J=8.7 Hz, 4H), 7.48 (s, 2H, N=CH), 7.39-7.19 (m, 10H), 7.18-7.07 (m, 6H), 7.07-7.00 (m, 1H), 6.93-6.84 (m, 2H), 3.88 (t, J=7.5 Hz, 4H), 1.75-1.59 (m, 4H), 1.49-1.18 (m, 24H), 0.88 (t, J=6.5 Hz, 6H, $CH_2CH_3$);

$^{13}$C NMR (75 MHz, $CDCl_3$, δ): 147.31, 147.18, 147.06, 131.48, 130.68, 129.28, 129.03, 126.86, 124.56, 123.96, 123.14, 119.98, 114.50, 45.23, 31.83, 29.53, 29.41, 29.23, 27.08, 24.81, 22.64, 14.09;

elemental analysis calcd (%) for $C_{50}H_{63}N_5$: C, 81.81; H, 8.65; N, 9.54. found: C, 81.89; H, 8.72; N, 9.55.

c) 4-[(N-nonyl-N-phenylhydrazin-2-ylmethyl)diphenylamino]benzaldehyde-N-(4-formyl)phenyl-N-nonylhydrazone (D9-3)

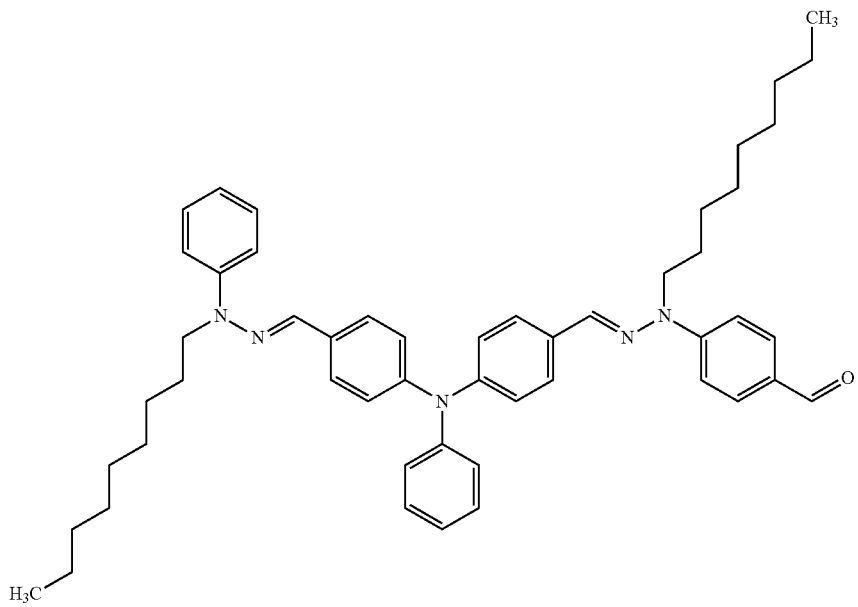 [SMILES: CCCCCCCCCN(/N=C/c1ccc(N(c2ccccc2)c2ccc(/C=N/N(CCCCCCCCC)c3ccc(C=O)cc3)cc2)cc1)c1ccccc1]

Phosphorus oxychloride (0.47 mL, 5.07 mmol) was added dropwise to DMF (2.85 mL, 37.03 mmol), not allowing the temperature of the mixture to rise above 5° C. A solution of D9-2 (2.48 g, 3.38 mmol) in DMF (6.0 mL) was added and the resulting mixture was heated at 60° C. for 2 h. The hot reaction mixture was poured into the ice water, neutralized by addition of sodium acetate (1.25 g, 15.23 mmol) aqueous solution, and extracted with ethyl acetate. The organic layer was dried over anhydrous Na$_2$SO$_4$, filtered, and the solvent evaporated. The crude product was purified by column chromatography using 3:22 v/v diethyl ether/n-hexane as an eluent to collect compound D9-3 as a yellow solid (0.21 g, 9%).

$^1$H NMR (300 MHz, CDCl$_3$, δ): 9.83 (s, 1H), 7.80 (d, J=8.9 Hz, 2H), 7.68-7.53 (m, 5H), 7.48 (s, 1H), 7.42 (d, J=8.9 Hz, 2H), 7.38-7.22 (m, 6H), 7.19-7.01 (m, 7H), 6.94-6.85 (m, 1H), 4.01-3.79 (m, 4H), 1.76-1.59 (m, 4H), 1.52-1.15 (m, 24H), 0.88 (t, J=6.5 Hz, 6H);

$^{13}$C NMR (75 MHz, CDCl$_3$, δ): 190.65, 151.48, 148.14, 147.13, 147.07, 146.73, 134.42, 131.93, 131.64, 130.50, 129.84, 129.38, 129.04, 128.32, 127.49, 126.91, 124.89, 124.38, 123.55, 123.27, 120.06, 114.52, 113.36, 45.25, 44.45, 31.83, 29.52, 29.48, 29.41, 29.35, 29.23, 29.20, 27.08, 26.98, 24.97, 24.79, 22.63, 14.09;

Anal. calcd for C$_{51}$H$_{63}$N$_5$O (%): C, 80.38; H, 8.33; N, 9.19. found: C, 80.40; H, 8.17; N, 9.11.

d) 4-[(N-nonyl-N-phenylhydrazin-2-ylmethyl)diphenylamino]benzaldehyde-N-4-(3-carboxymethyl-4-oxo-2-thioxo-1,3-thiazolidin-5-ylidenmethyl)phenyl-N-nonylhydrazone (D9)

A mixture of D9-3 (0.16 g, 0.21 mmol), rhodanine-3-acetic acid (0.05 g, 0.25 mmol) and ammonium acetate (0.05 g, 0.06 mmol) was refluxed in acetic acid (3.5 mL) for 3 h. Afterwards, water (15 mL) was added and the extraction was done with ethyl acetate. The organic layer was dried over anhydrous Na$_2$SO$_4$, filtered, and solvent evaporated. The crude product was purified by column chromatography using 1:24 v/v methanol/toluene as an eluent to collect dye D9 as a dark red solid (0.08 g, 41%).

$^1$H NMR (300 MHz, CDCl$_3$, δ): 7.72-6.73 (m, 25H), 4.82 (s, 2H), 3.96-3.69 (m, 4H), 1.74-1.49 (m, 4H), 1.44-1.07 (m, 24H), 0.93-0.71 (m, 6H);

$^{13}$C NMR (75 MHz, CDCl$_3$, δ): 192.84, 187.16, 176.62, 165.24, 147.08, 134.05, 133.45, 130.09, 129.65, 129.38, 129.04, 127.60, 127.38, 127.07, 126.91, 126.04, 124.89, 124.34, 120.07, 114.53, 114.13, 45.25, 31.83, 29.53, 29.41, 29.23, 27.08, 24.81, 22.64, 14.10;

IR (KBr): ν=3481 (OH); 3059, 3030 (aromatic CH); 2951, 2923, 2851 (aliphatic CH); 1708 (C=O); 1577, 1505, 1495 (C=C); 1284 (C=S); 1201, 1187, 1179, 1121, 1103 (C—N); 892, 823 (CH=CH of 1,4-disubstituted benzenes), 747, 722, 693 (CH=CH of monosubstituted benzenes);

Anal. calcd for C$_{56}$H$_{66}$N$_6$O$_3$S$_2$(%): C, 71.91; H, 7.11; N, 8.99. found: C, 71.83; H, 6.98; N, 8.84.

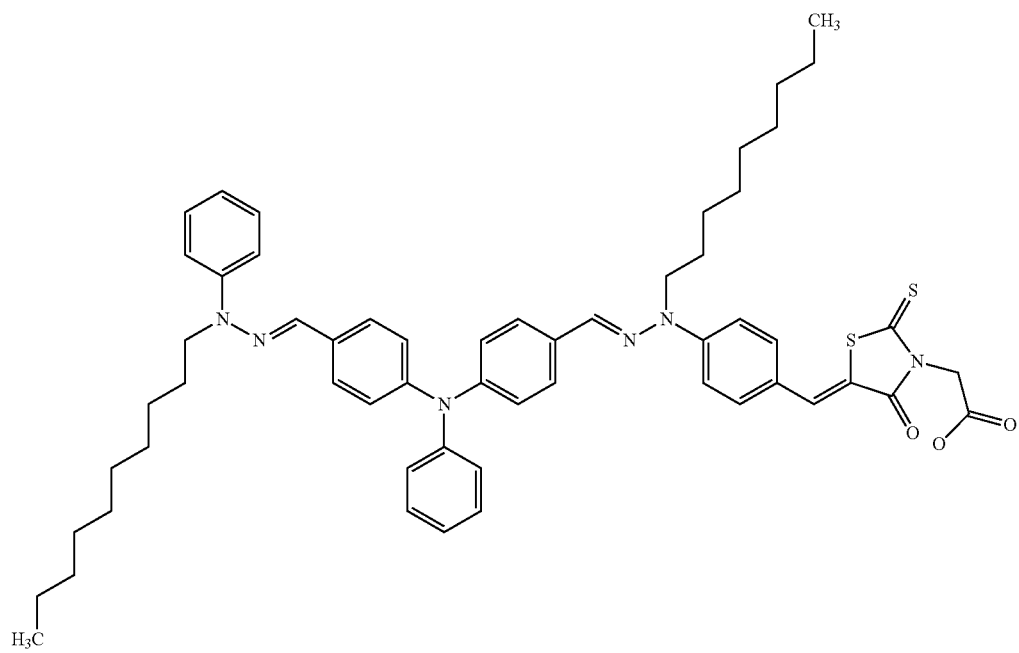 [SMILES: CCCCCCCCCCN(/N=C/c1ccc(N(c2ccccc2)c2ccc(/C=N/N(CCCCCCCCC)c3ccc(/C=C4\SC(=S)N(CC(=O)O)C4=O)cc3)cc2)cc1)c1ccccc1]

A3) Preparation of Dyes D10 to D12

Preparation of Dye D10 a) 4-(diphenylamino)benzaldehyde-N-(7-chloroquinolin-4-yl)hydrazone (D10-1)

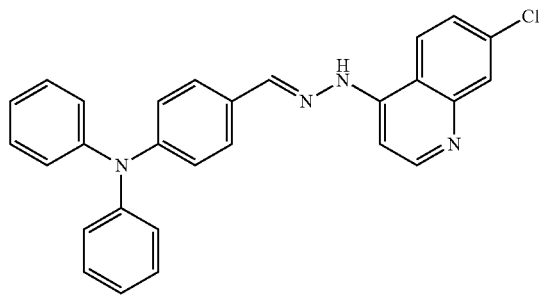 [SMILES: Clc1ccc2c(N/N=C/c3ccc(N(c4ccccc4)c4ccccc4)cc3)ccnc2c1]

To 4-(diphenylamino)benzaldehyde (1.0 g, 3.66 mmol; corresponds to compound 1 where both radicals R equal phenyl), dissolved in toluene (15 mL), 7-chloro-4-hydrazinoquinoline (1.0 g, 5.16 mmol), dissolved in methanol (30 ml), was added. The mixture was refluxed until the arylaldehyde disappeared (TLC, acetone:n-hexane=7:18). Afterwards, the mixture was cooled to room temperature. Yellow crystals of 9 (1.41 g, 86%), having formed upon standing, were filtered off and washed with a mixture of 2-propanol and n-hexane (1:2). The crude product was used in the next step without additional purification.

b) 4-(diphenylamino)benzaldehyde-N-(4-formyl)phenyl-N-(7-chloroquinolin-4-yl)hydrazone (D10-2)

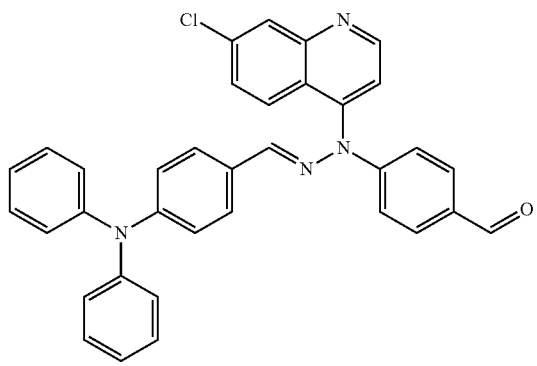 [SMILES: O=Cc1ccc(N(/N=C/c2ccc(N(c3ccccc3)c3ccccc3)cc2)c2ccnc3cc(Cl)ccc23)cc1]

A mixture of D10-1 (1.41 g, 3.15 mmol), 4-fluorobenzaldehyde (1.0 mL, 9.32 mmol) and K$_2$CO$_3$ (2.60 g, 18.81 mmol) was refluxed in 20 mL anhydrous DMF under argon atmosphere for 1.5 h. Afterwards, the mixture was cooled to room temperature, water (30 mL) was added and the extraction was done with chloroform. The organic layer was washed with water, dried over anhydrous Na$_2$SO$_4$ and filtered. Light orange crystals, having formed after evaporation of the solvent, were filtered off and washed with 2-propanol to give the corresponding arylaldehyde D10-2 (1.13 g, 65%).

$^1$H NMR (300 MHz, CDCl$_3$): δ=10.09 (s, 1H, CHO), 8.54-8.47 (m, 2H), 8.08 (d, J=8.5 Hz, 2H), 7.68 (d, J=8.7 Hz, 2H), 7.56 (d, J=8.3 Hz, 2H), 7.32-7.00 (m, 14H), 6.96 (d, J=8.1 Hz, 1H), 6.82 (d, J=1.9 Hz, 1H);

$^{13}$C NMR (75 MHz, CDCl$_3$): δ=190.52, 155.46, 154.81, 149.37, 147.12, 146.38, 139.98, 136.44, 136.07, 131.67, 129.32, 129.13, 128.82, 128.15, 126.70, 125.01, 124.37, 123.52, 122.20, 121.13, 115.43, 101.72;

IR (KBr): ν=3065 (aromatic CH); 2957, 2915, 2845, 2742 (aliphatic CH); 1697 (C=O); 1626, 1594, 1492, 1436, 1399 (C=C); 1187, 1174, 1143, 1117, 1105, 1078 (C—N); 857, 837, 805 (CH=CH of 1,4-disubstituted benzenes); 751, 727, 711, 694 (CH=CH of monosubstituted benzenes);

Anal. calcd for C$_{35}$H$_{25}$ClN$_4$O (%): C, 76.01; H, 4.56; N, 10.13. found: C, 75.98; H, 4.53; N, 10.11.

c) 4-(diphenylamino)benzaldehyde-N-4-(3-carboxymethyl-4-oxo-2-thioxo-1,3-thiazolidin-5-ylidenmethyl)phenyl-N-(7-chloro-4-quinolin-4-yl)hydrazone (D10)

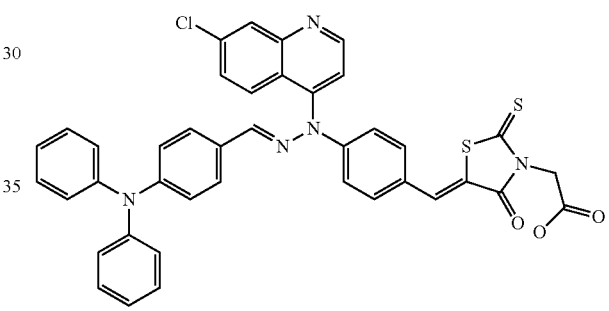

A mixture of D10-2 (0.4 g, 0.72 mmol), rhodanine-3-acetic acid (0.17 g, 0.87 mmol), and ammonium acetate (0.02 g, 0.22 mmol) was refluxed in acetic acid (3 mL) for 50 min. At the end of the reaction, the mixture was cooled to room temperature. Dark orange crystals, having formed upon standing, were filtered off and washed with water, methanol and finally with diethyl ether to give dye D10 (0.4 g, 76%).

$^1$H NMR (300 MHz, 50% DMSO-d$_6$/CDCl$_3$): δ=8.53-8.39 (m, 2H), 7.97 (s, 1H), 7.89 (d, J=8.1 Hz, 2H), 7.80-7.58 (m, 4H), 7.55-7.24 (m, 6H), 7.23-7.01 (m, 7H), 6.97 (d, J=8.4 Hz, 2H), 6.87 (s, 1H), 4.75 (s, 2H);

IR (KBr): ν=3408 (OH); 3060, 3034 (aromatic CH); 2923 (aliphatic CH); 1715 (C=O); 1617, 1589, 1523, 1505, 1490 (C=C); 1291 (C=S); 1197, 1176, 1123, 1101, 1076 (C—N); 895, 857, 823 (CH=CH of 1,4-disubstituted benzenes); 753, 729, 696 (CH=CH of monosubstituted benzenes);

Anal. calcd for C$_{40}$H$_{28}$ClN$_5$O$_3$S$_2$(%): C, 66.15; H, 3.89; N, 9.64. found: C, 66.21; H, 3.90; N, 9.71.

Preparation of Dye D11 a) 1-Phenyl-3-propoxy-1,2,3,4-tetrahydroquinoline-6-carbaldehyde (D11-1)

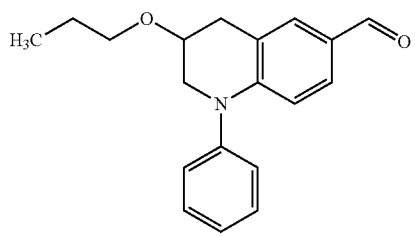 [SMILES: CCCOC1Cc2cc(C=O)ccc2N(c2ccccc2)C1]

Compound D11-1 was prepared according to T. Malinauskas, J. Stumbraite, V. Getautis, V. Gaidelis, V. Jankauskas, G. Juska, K. Arlauskas, K. Kazlauskas Dyes and Pigments 81 (2009) 131-136.

b) 1-Phenyl-3-propoxy-1,2,3,4-tetrahydroquinoline-6-carbaldehyde-N-phenylhydrazone (D11-2)

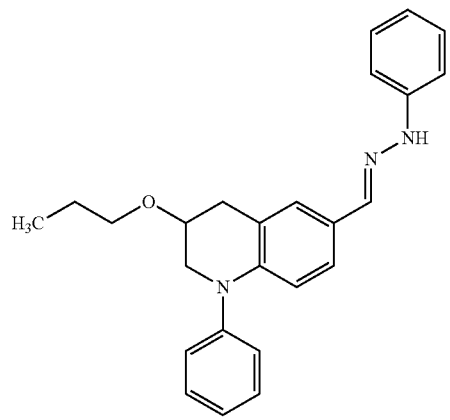 [SMILES: CCCOC1Cc2cc(/C=N/Nc3ccccc3)ccc2N(c2ccccc2)C1]

To compound 011-2 (5.00 g, 17.77 mmol) dissolved in 2-propanol (25 mL), phenylhydrazine (2.31 mL, 21.31 mmol) was added. The mixture was refluxed for 1 h until the arylaldehyde disappeared (TLC, v/v diethylether/n-hexane, 2:3). At the end of the reaction, the mixture was cooled to room temperature. Yellow crystals, having formed upon standing, were filtered off and washed with a mixture of 2-propanol and n-hexane (1:2) to give the corresponding phenylhydrazone 25 (6.5 g, 99%), which was used in the next reaction without further purification.

c) 1-Phenyl-3-propoxy-1,2,3,4-tetrahydroquinoline-6-carbaldehyde-N-(4-formyl)phenyl-N-phenylhydrazone (011-3)

A mixture of compound D11-2 (6.5 g, 16.86 mmol), 4-fluorobenzaldehyde (3.14 g, 25.29 mmol), and $K_2CO_3$ (6.99 g, 50.58 mmol) were refluxed in anhydrous DMF (35 mL) under argon atmosphere for 20 h. After cooling to room temperature, distilled water (30 mL) was added and mixture was extracted with ethyl acetate, dried over anhydrous $Na_2SO_4$, filtered and solvent was evaporated. The crude product was purified by column chromatography using 2:23 v/v acetone/n-hexane as an eluent to collect compound D11-3 as a yellow solid (5.28 g, 64%).

$^1$H NMR (300 MHz, CDCl$_3$, δ): 9.80 (s, 1H), 7.72 (d, J=9.0 Hz, 2H), 7.62 (t, J=7.4 Hz, 2H), 7.52 (t, J=7.4 Hz, 1H), 7.41-7.31 (m, 3H), 7.28-7.09 (m, 9H), 6.68 (d, J=8.6 Hz, 1H), 3.98-3.86 (m, 1H), 3.83-3.73 (m, 1H), 3.61-3.39 (m, 3H), 3.15 (dd, J=15.7, 4.6 Hz, 1H), 2.89 (dd, J=15.9, 7.9 Hz, 1H), 1.65-1.50 (m, 2H), 0.89 (t, J=7.4 Hz, 3H);

$^{13}$C NMR (75 MHz, CDCl$_3$, δ): 190.89, 152.38, 147.35, 145.22, 140.12, 138.77, 131.58, 131.21, 130.14, 129.72, 129.43, 128.79, 128.55, 125.86, 125.60, 125.13, 124.63, 122.17, 115.10, 114.07, 71.33, 70.60, 54.17, 34.40, 23.39, 10.78;

Anal. calcd. for $C_{32}H_{31}N_3O_2$(%): C, 78.50; H, 6.38; N, 8.58. found: C, 78.41; H, 6.52; N, 8.63.

d) 1-Phenyl-3-propoxy-1,2,3,4-tetrahydroquinoline-6-carbaldehyde-N-4-(3-carboxymethyl-4-oxo-2-thioxo-1,3-thiazolidin-5-ylidenmethyl)phenyl-N-phenylhydrazone (D11)

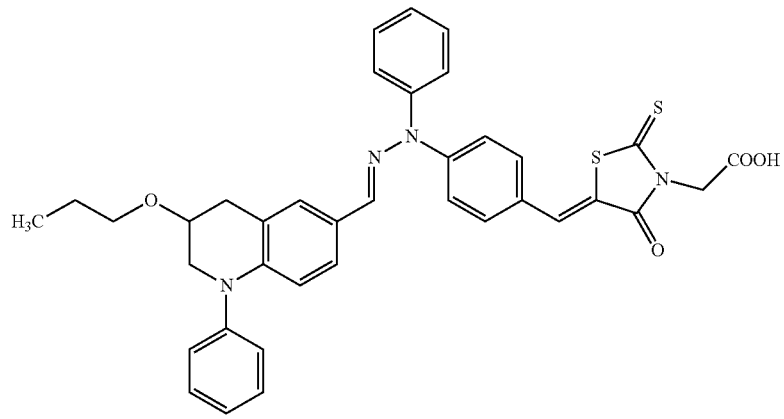 [SMILES: CCCOC1Cc2cc(/C=N/N(c3ccccc3)c3ccc(/C=C4\SC(=S)N(CC(=O)O)C4=O)cc3)ccc2N(c2ccccc2)C1]

A mixture of compound D11-3 (0.99 g, 2.03 mmol), rhodanine-3-acetic acid (0.46 g, 2.43 mmol) and ammonium acetate (0.05 g, 0.61 mmol) was refluxed in acetic acid (3.0 mL) for 2 h. Afterwards, water (15 mL) was added and the extraction was done with chloroform. The organic layer was dried over anhydrous $Na_2SO_4$, filtered, and solvent evaporated. The crude product was purified by column chromatography using 2:23 v/v methanol/toluene as an eluent to collect dye D11 as a dark red solid (0.81 g, 61%).

$^1$H NMR (300 MHz, $CDCl_3$, δ): 7.82-7.05 (m, 17H), 6.72 (dd, J=8.5, 6.2 Hz, 1H), 6.41 (d, J=8.9 Hz, 1H), 4.89 (s, 2H), 4.04-3.89 (m, 1H), 3.89-3.41 (m, 4H), 3.27-2.84 (m, 2H), 1.71-1.52 (m, 2H), 1.03-0.83 (m, 3H);

Anal. calcd for $C_{37}H_{34}N_4O_4S_2$(%): C, 67.05; H, 5.17; N, 8.45. found: C, 67.17; H, 5.31; N, 8.58.

Preparation of Dye D12 a) 1,2,3,3a,4,8b-hexahydro-4-[4-(2,2-diphenylethenyl)phenyl]cyclopenta[b]indole-7-carboxaldehyde (D12-1)

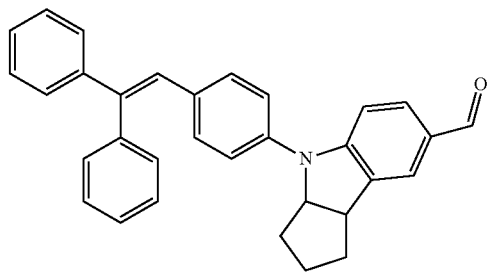 [SMILES: O=Cc1ccc2c(c1)C1CCCC1N2c1ccc(C=C(c2ccccc2)c2ccccc2)cc1]

Prepared according to published Japanese patent application JP 2010-083767.

b) 1,2,3,3a,4,8b-hexahydro-4-[4-(2,2-diphenylethenyl)phenyl]cyclopenta[b]indole-7-carboxaldehyde-N-phenylhydrazone (D12-2)

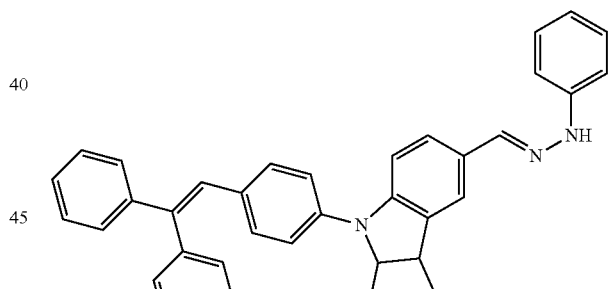

To compound D12-1 (1.50 g, 3.39 mmol) dissolved in toluene (8 mL) and 2-propanol (4 mL), phenylhydrazine (0.40 mL, 4.08 mmol) was added. The mixture was refluxed for 2.5 h until the arylaldehyde disappeared (TLC, toluene). At the end of the reaction, the mixture was cooled to room temperature. Yellow crystals, having formed upon standing, were filtered off and washed with 2-propanol to give the corresponding phenylhydrazone D12-2 (1.42 g, 79%), which was used in the next reaction without further purification.

c) 1,2,3,3a,4,8b-hexahydro-4-[4-(2,2-diphenylethenyl)phenyl]cyclopenta[b]indole-7-carboxaldehyde-N-(4-formyl)phenyl-N-phenylhydrazone (D12-3)

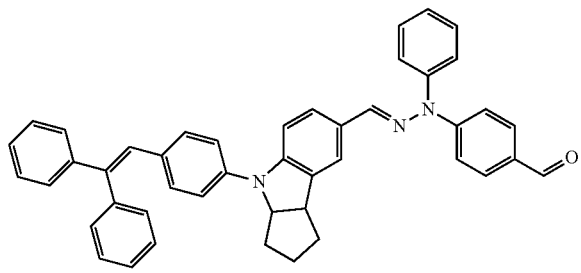 [SMILES: O=Cc1ccc(N(/N=C/c2ccc3c(c2)C2CCCC2N3c2ccc(C=C(c3ccccc3)c3ccccc3)cc2)c2ccccc2)cc1]

A mixture of compound D12-2 (1.3 g, 2.45 mmol), 4-fluorobenzaldehyde (0.45 g, 3.7 mmol), and $K_2CO_3$ (1.02 g, 7.34 mmol) were refluxed in anhydrous DMF (25 mL) under argon atmosphere for 5 h (TLC, toluene). After cooling to room temperature, distilled water (30 mL) was added and mixture was extracted with ethyl acetate, dried over anhydrous $Na_2SO_4$, filtered and solvent was evaporated. The crude product was purified by column chromatography using 2:2:21 v/v acetone/THF/n-hexane as an eluent to collect compound D12-3 as a yellow solid (0.86 g, 55%).

$^1$H NMR (300 MHz, $CDCl_3$, δ): 9.98 (s, 1H), 7.93 (d, J=8.7 Hz, 2H), 7.74 (d, J=8.9 Hz, 2H), 7.64 (t, J=7.4 Hz, 2H), 7.60-7.50 (m, 2H), 7.50-7.12 (m, 16H), 7.11-6.88 (m, 4H), 4.86-4.66 (m, 1H), 3.96-3.70 (m, 1H), 2.15-1.36 (m, 6H);
$^{13}$C NMR (75 MHz, $CDCl_3$, δ): 190.87, 161.26, 152.46, 148.16, 143.81, 141.28, 140.97, 140.43, 138.88, 136.31, 132.85, 132.33, 131.67, 131.30, 130.96, 130.68, 130.62, 130.26, 129.52, 129.05, 128.62, 128.44, 128.03, 127.85, 127.63, 127.49, 126.44, 122.66, 119.63, 118.53, 114.15, 108.29, 69.10, 45.36, 35.12, 34.10, 24.63; Anal. calcd. for $C_{45}H_{37}N_3O$ (%): C, 85.01; H, 5.87; N, 6.61. found: C, 85.25; H, 5.72; N, 6.59.

d) 1,2,3,3a,4,8b-hexahydro-4-[4-(2,2-diphenylethenyl)phenyl]cyclopenta[b]indole-7-carboxaldehyde-N-4-(3-carboxymethyl-4-oxo-2-thioxo-1,3-thiazolidin-5-yliden-methyl)phenyl-N-phenylhydrazone (D12)

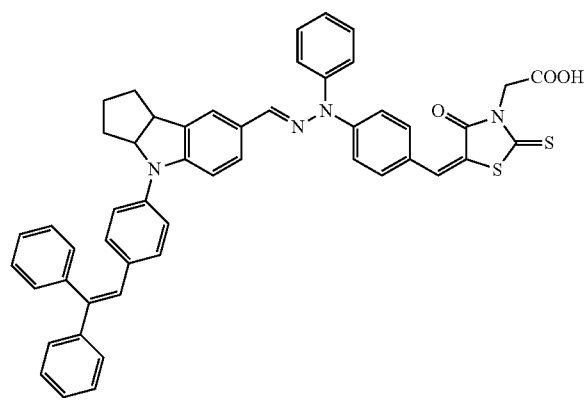 [SMILES: O=C(O)CN1C(=O)/C(=C\c2ccc(N(/N=C/c3ccc4c(c3)C3CCCC3N4c3ccc(C=C(c4ccccc4)c4ccccc4)cc3)c3ccccc3)cc2)SC1=S]

A mixture of compound D12-3 (0.205 g, 0.32 mmol), rhodanine-3-acetic acid (0.074 g, 0.39 mmol) and ammonium acetate (0.015 g, 0.19 mmol) was refluxed in acetic acid (3.0 mL) for 6.5 h. Afterwards, water (15 mL) was added and the extraction was done with chloroform. The organic layer was dried over anhydrous $Na_2SO_4$, filtered, and solvent evaporated. The crude product was purified by column chromatography using 47:3 v/v toluene/methanol as an eluent to collect dye D12 as a dark red solid (0.125 g, 48%).

$^1$H NMR (300 MHz, $CDCl_3$, δ): 7.74-7.47 (m, 3H), 7.45-7.08 (m, 20H), 7.06-6.80 (m, 6H), 4.95-4.66 (m, 3H), 3.97 (dd, J=7.5, 5.8 Hz, 1H), 2.14-1.71 (m, 6H);
Anal. calcd. for $C_{50}H_{40}N_4O_3S_2$(%): C, 74.23; H, 4.98; N, 6.93. found: C, 74.50; H, 5.11; N, 6.69.

B) Preparation and Characterization of the DSCs

General Methods and Materials

Preparation of the (solid-state) DSCs: A $TiO_2$ blocking layer was prepared on a fluorine-doped tin oxide (FTO)-covered glass substrate using spray pyrolysis (cf. B. Peng, G. Jungmann, C. Jager, D. Haarer, H. W. Schmidt, M. Thelakkat, Coord. Chem. Rev. 2004, 248, 1479). Next, a $TiO_2$ paste (Dyesol), diluted with terpineol, was applied by screen printing, resulting in a film thickness of 1.7 μm. All films were then sintered for 45 min at 450° C., followed by treatment in a 40 mM aqueous solution of $TiCl_4$ at 60° C. for 30 min, followed by another sintering step. The prepared samples with $TiO_2$ layers were pretreated with 5 mM solutions of the additives 2-(p-butoxyphenyl)acetohydroxamic acid ("ADD3"), 2-(p-butoxyphenyl)acetohydroxamic acid sodium salt ("ADD1") or 2-(p-butoxyphenyl)acetohydroxamic acid tetrabutylammonium salt ("ADD2") in ethanol (these additives are described on pages 52 and 53 of WO 2012/001628 A1 as "Example No. 5", "Example No. 6" and "Example No. 10", respectively). The electrodes were then dyed in 0.5 mM dye solution in $CH_2Cl_2$. Spiro-MeOTAD was applied by spin-coating from a solution in DCM (200 mg/mL) also containing 20 mM $Li(CF_3SO_2)_2N$. Fabrication of the device was completed by evaporation of 200 nm of silver as the counter electrode. The active area of the sDSC was defined by the size of these contacts (0.13 cm$^2$), and the cells were masked by an aperture of the same area for measurements. The current-voltage characteristics for all cells were measured with a Keithley 2400 under 1000 W/m$^2$, AM 1.5G conditions (LOT ORIEL 450 W). The incident photon to current conversion efficiency's (IPCE) were obtained with an Acton Research Monochromator using additional white background light illumination.

The samples were illuminated with monochromatic light from the quartz monochromator with deuterium lamp. The power of the incident light beam was (2-5)·10$^{-8}$ W. The negative voltage of −300 V was supplied to the sample substrate. The counter-electrode with the 4.5×15 mm$^2$ slit for illumination was placed at 8 mm distance from the sample surface. The counter-electrode was connected to the input of the BK2-16 type electrometer, working in the open input regime, for the photocurrent measurement. The 10$^{-15}$-10$^{-12}$ A strong photocurrent was flowing in the circuit under illumination. The photocurrent J is strongly dependent on the incident light photon energy hv. The $J^{0.5}$=f(hv) dependence was plotted. Usually the dependence of the photocurrent on incident light quanta energy is well described by linear relationship between $J^{0.5}$ and hv near the threshold (cf. E. Miyamoto, Y. Yamaguchi, M. Yokoyama, Electrophotography 1989, 28, 364 and M. Cordona, L. Ley, Top. Appl. Phys. 1978, 26, 1). The linear part of this dependence was extrapolated to the hν axis and $J_p$ value was determined as the photon energy at the interception point.

The results of the DSCs with varying dyes and additives are given in the following table 1.

TABLE 1

Photovoltaic performance of sDSCs based on the D1-D12 dyes

| Dye | Additive | $J_{SC}$ [mA cm$^{-2}$] | $V_{OC}$ [mV] | FF [%] | η [%] |
|-----|----------|-------------------------|---------------|--------|-------|
| D1  | ADD1     | 7.34                    | 680           | 51     | 2.5   |
| D1  | ADD3     | 6.86                    | 560           | 57     | 2.2   |
| D2  | ADD1     | 7.82                    | 760           | 62     | 3.7   |
| D2  | ADD2     | 6.9                     | 580           | 55     | 2.2   |
| D3  | ADD1     | 7.00                    | 800           | 64     | 3.6   |
| D3  | ADD2     | 8.04                    | 660           | 58     | 3.1   |
| D4  | ADD1     | 6.51                    | 840           | 64     | 3.5   |
| D4  | ADD2     | 7.28                    | 840           | 62     | 3.8   |
| D8  | ADD1     | 2.76                    | 740           | 56     | 1.1   |
| D8  | ADD2     | 3.42                    | 780           | 58     | 1.5   |
| D9  | ADD1     | 5.3                     | 800           | 74     | 3.1   |
| D9  | ADD2     | 4.18                    | 760           | 69     | 2.2   |
| D11 | ADD1     | 6.08                    | 780           | 68     | 3.2   |
| D11 | ADD2     | 6.9                     | 720           | 66     | 3.3   |
| D12 | ADD1     | 7.68                    | 680           | 61     | 3.2   |
| D12 | ADD2     | 7.71                    | 740           | 63     | 3.6   |

The invention claimed is:

1. A compound represented by formula (I):

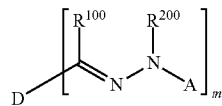

(I)

wherein
$R^{100}$ and $R^{200}$ are each independently hydrogen, $C_1$-$C_{10}$-alkyl which in case of $C_2$-alkyl may be interrupted by one and in case of $C_3$-$C_{10}$-alkyl by one or two nonadjacent oxygen atoms, $C_5$-$C_7$-cycloalkyl, aryl, aryl-$C_1$-$C_{10}$-alkyl or aryloxy-$C_1$-$C_{10}$-alkyl, D is an m-valent donor moiety which comprises at least one carbon-carbon or carbon-heteroatom double bond and/or at least one unfused or fused carbo- or heterocyclic ring, A is an acceptor moiety which comprises at least one carbon-carbon or carbon-heteroatom double bond and/or at least one unfused or fused carbo- or heterocyclic ring, m is 1, 2 or 3, the donor moiety D and the acceptor moiety A are π-conjugated to one another, when m=1 the donor moiety D is selected from the group consisting of:

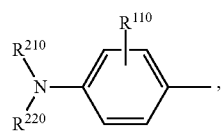

(D01)

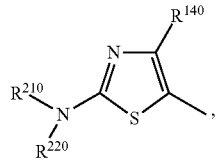

(D02)

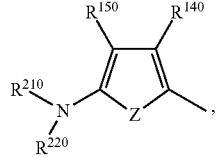

(D03)

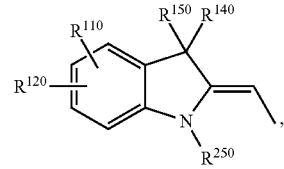

(D04)

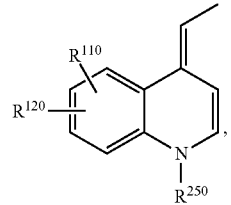

(D05)

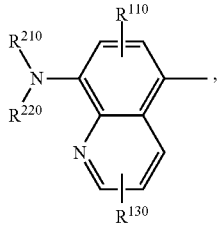

(D06)

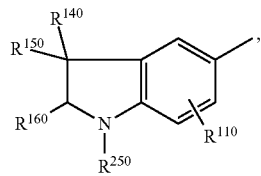

(D07)

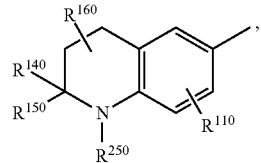

(D08)

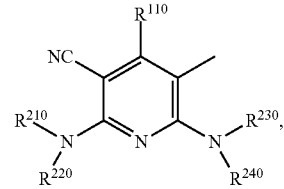

(D09)

-continued (D10)

(D11)

(D12)

(D13) and (D14)

$R^{110}$, $R^{120}$ and $R^{130}$ independently hydrogen, halogen, hydroxyl, $C_1$-$C_{10}$-alkyl which in case of $C_2$-alkyl may be interrupted by one and in case of $C_3$-$C_{10}$-alkyl by one or two nonadjacent oxygen atoms, $C_5$-$C_7$-cycloalkyl, $C_1$-$C_{10}$-alkoxy, $C_1$-$C_{10}$-alkylamino, di($C_1$-$C_{10}$-alkyl)amino, $C_1$-$C_{10}$-alkylamino- or di($C_1$-$C_{10}$-alkyl)aminosulfonylamino, $C_1$-$C_{10}$-alkylsulfonylamino, aryl, aryl-$C_1$-$C_{10}$-alkyl, aryloxy-$C_1$-$C_{10}$-alkyl or an —NHCOR$^{170}$ or —NHCOOR$^{170}$ radical, $R^{140}$, $R^{150}$ and $R^{160}$ are each independently hydrogen, $C_1$-$C_{10}$-alkyl which in case of $C_2$-alkyl may be interrupted by one and in case of $C_3$-$C_{10}$-alkyl by one or two nonadjacent oxygen atoms, $C_5$-$C_7$-cycloalkyl, aryl aryl-$C_1$-$C_{10}$-alkyl, aryloxy-$C_1$-$C_{10}$-alkyl or in case $R^{140}$ and $R^{160}$ or $R^{150}$ and $R^{160}$ are bonded to adjacent carbon atoms these pairs of groups may—together with the carbon atoms to which they are bonded—form a five- or six-membered ring in which one CH$_2$ group may be replaced by an oxygen atom, $R^{170}$ is aryl, aryl-$C_1$-$C_{10}$-alkyl, aryloxy-$C_1$-$C_{10}$-alkyl or $C_1$-$C_{10}$-alkyl which in case of $C_2$-alkyl may be interrupted by one and in case of $C_3$-$C_{10}$-alkyl by one or two nonadjacent oxygen atoms and in case of two moities for m=2 may vary independently of each other, $R^{210}$, $R^{220}$, $R^{230}$ and $R^{240}$ are each independently aryl, aryl-$C_1$-$C_{10}$-alkyl, aryloxy-$C_1$-$C_{10}$-alkyl, $C_1$-$C_{10}$-alkyl which in case of $C_2$-alkyl may be interrupted by one and in case of $C_3$-$C_{10}$-alkyl by one or two nonadjacent oxygen atoms, $C_5$-$C_{10}$-cycloalkyl, or $R^{210}$ and $R^{220}$ and/or $R^{230}$ and $R^{240}$ form, together with the nitrogen atom to which they are bonded, a five- or six-membered ring in which one CH$_2$ group not adjacent to the nitrogen atom may be replaced by an oxygen atom, or in case NR$^{210}$R$^{220}$ and R$^{110}$ are bonded to adjacent carbon atoms, $R^{110}$ and $R^{210}$ or $R^{110}$ and $R^{220}$—together with the nitrogen atom of the moiety NR$^{210}$R$^{220}$ and the carbon atom to which the moieties NR$^{210}$R$^{220}$ and $R^{110}$ are bonded—form a five- or six-membered ring in which one CH$_2$ group not adjacent to the nitrogen atom may be replaced by an oxygen atom and which five- or six-membered ring may be fused to another five- or six-membered saturated or unsaturated ring, $R^{250}$ and $R^{260}$ are each independently $C_1$-$C_{10}$-alkyl which in case of $C_2$-alkyl may be interrupted by one and in case of $C_3$-$C_{10}$-alkyl by one or two nonadjacent oxygen atoms, $C_5$-$C_7$-cycloalkyl, aryl, aryl-$C_1$-$C_{10}$-alkyl or aryloxy-$C_1$-$C_{10}$-alkyl, Z is O or S, when m=2 the donor moiety D is selected from the group consisting of:

wherein $R^{170}$ is defined above and in case of two moieties may vary independently of each other, when m=3 the donor moiety D is selected from the group consisting of:

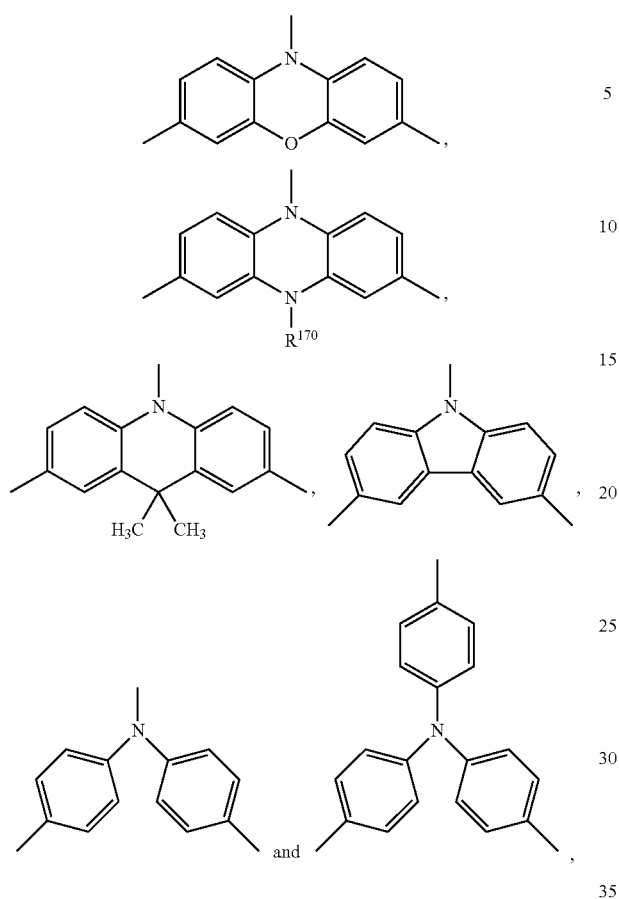

wherein R¹⁷⁰ is defined above,

A is represented by formula (Ia):

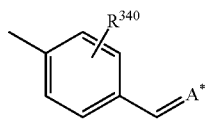

(Ia)

A* represents a moiety selected from the group consisting of:

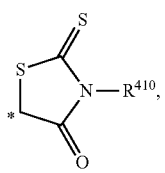

(A01)

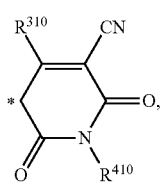

(A02)

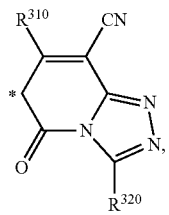

(A03)

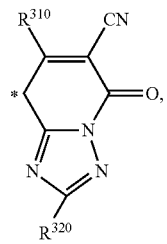

(A04)

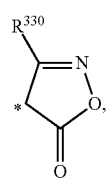

(A05)

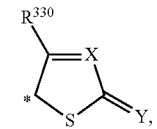

(A06)

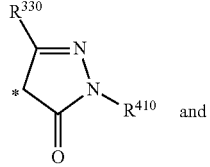

(A07)

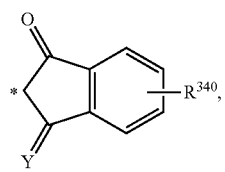

(A08)

* indicates the position which the double bond of the group of formula (Ia) is bonded to, R³¹⁰ and R³²⁰ are each independently hydrogen, $C_1$-$C_{10}$-alkyl which in case of $C_2$-alkyl may be interrupted by one and in case of $C_3$-$C_{10}$-alkyl by one or two nonadjacent oxygen atoms, or $C_5$-$C_7$-cycloalkyl, R³³⁰ is hydrogen, $C_1$-$C_{10}$-alkyl which in case of $C_2$-alkyl may be interrupted by one and in case of $C_3$-$C_{10}$-alkyl by one or two nonadjacent oxygen atoms, partly fluorinated $C_1$-$C_{10}$-alkyl, perfluorinated $C_1$-$C_{10}$-alkyl, $C_5$-$C_7$-cycloalkyl, aryl, aryl-$C_1$-$C_{10}$-alkyl or aryloxy-$C_1$-$C_{10}$-alkyl, R³⁴⁰ is hydrogen, $NO_2$, CN, $COR^{350}$, $COOR^{350}$, $SO_2R^{350}$ or $SO_3R^{350}$, R³⁵⁰ is aryl, aryl-$C_1$-$C_{10}$-alkyl, aryloxy-$C_1$-$C_{10}$-alkyl or $C_1$-$C_{10}$-alkyl which in case of $C_2$-alkyl may be interrupted by one and in case of $C_3$-$C_{10}$-alkyl by one or two nonadjacent oxygen atoms, R⁴¹⁰ is hydrogen, $C_1$-$C_{10}$-alkyl which in case of $C_2$-alkyl may be interrupted by one and in case of $C_3$-$C_{10}$-alkyl by one or two nonadjacent oxygen atoms and which may be mono- or polysubstituted by hydroxyl, mercapto, halogen, cyano, nitro, —COOM and/or —COOR$^{420}$, $C_5$-$C_7$-cycloalkyl, aryl, aryl-$C_1$-$C_{10}$-alkyl, aryloxy-$C_1$-$C_{10}$-alkyl, or an —NHCOR$^{420}$ or —N(COR$^{420}$)$_2$ radical where the two R$^{420}$ in the latter may be the same or different, X is independently CH or N, Y is O, C(CN)$_2$, C(CN)(COOM) or C(CN)(COOR$^{420}$), M is alkali metal cation or [NR$^{420}$]$_4^+$, and R$^{420}$ is hydrogen, aryl, aryl-$C_1$-$C_{10}$-alkyl, aryloxy-$C_1$-$C_{10}$-alkyl or $C_1$-$C_{10}$-alkyl which in case of $C_2$-alkyl may be interrupted by one and in case of $C_3$-$C_{10}$-alkyl by one or two nonadjacent oxygen atoms.

2. The compound of claim 1, wherein
R$^{100}$ is hydrogen or $C_1$-$C_4$-alkyl, and
R$^{200}$ is aryl or $C_1$-$C_{10}$-alkyl which in case of $C_2$-alkyl may be interrupted by one and in case of $C_3$-$C_{10}$-alkyl by one or two nonadjacent oxygen atoms.

3. The compound of claim 1, wherein
when m=1 the donor moiety D is selected from the group consisting of:

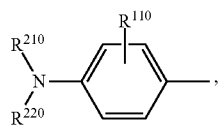
(D01)

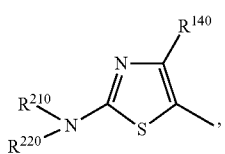
(D02)

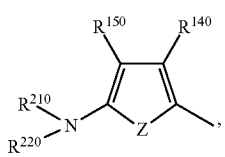
(D03)

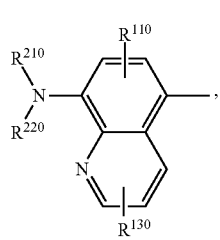
(D06)

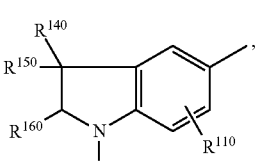
(D07)

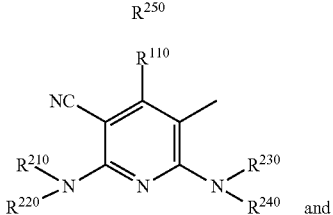
(D09)

and

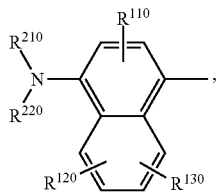
(D14)

R$^{110}$, R$^{120}$ and R$^{130}$ are each independently hydrogen, halogen, hydroxyl, $C_1$-$C_{10}$-alkyl which in case of $C_2$-alkyl may be interrupted by one and in case of $C_3$-$C_{10}$-alkyl by one or two nonadjacent oxygen atoms, $C_5$-$C_7$-cycloalkyl, $C_1$-$C_{10}$-alkoxy, $C_1$-$C_{10}$-alkylamino, di($C_1$-$C_{10}$-alkyl)amino, $C_1$-$C_{10}$-alkylamino- or di($C_1$-$C_{10}$-alkyl)aminosulfonylamino, $C_1$-$C_{10}$-alkylsulfonylamino, aryl, aryl-$C_1$-$C_{10}$-alkyl, aryloxy-$C_1$-$C_{10}$-alkyl or an —NHCOR$^{170}$ or —NHCOOR$^{170}$ radical, R$^{140}$, R$^{150}$ and R$^{160}$ are each independently hydrogen, $C_1$-$C_{10}$-alkyl which in case of $C_2$-alkyl may be interrupted by one and in case of $C_3$-$C_{10}$-alkyl by one or two nonadjacent oxygen atoms, $C_5$-$C_7$-cycloalkyl, aryl aryl-$C_1$-$C_{10}$-alkyl, aryloxy-$C_1$-$C_{10}$-alkyl or in case R$^{140}$ and R$^{160}$ or R$^{150}$ and R$^{160}$ are bonded to adjacent carbon atoms these pairs of groups may—together with the carbon atoms to which they are bonded-form a five- or six-membered ring in which one CH$_2$ group may be replaced by an oxygen atom, R$^{170}$ is aryl, aryl-$C_1$-$C_{10}$-alkyl, aryloxy-$C_1$-$C_{10}$-alkyl or $C_1$-$C_{10}$-alkyl which in case of $C_2$-alkyl may be interrupted by one and in case of $C_3$-$C_{10}$-alkyl by one or two nonadjacent oxygen atoms and in case of two moieties for m=2 may vary independently of each other, R$^{210}$, R$^{220}$, R$^{230}$ and R$^{240}$ are each independently aryl, aryl-$C_1$-$C_{10}$-alkyl, aryloxy-$C_1$-$C_{10}$-alkyl, $C_1$-$C_{10}$-alkyl which in case of $C_2$-alkyl may be interrupted by one and in case of $C_3$-$C_{10}$-alkyl by one or two nonadjacent oxygen atoms, $C_5$-$C_{10}$-cycloalkyl, or R$^{210}$ and R$^{220}$ and/or R$^{230}$ and R$^{240}$ form, together with the nitrogen atom to which they are bonded, a five- or six-membered ring in which one CH$_2$ group not adjacent to the nitrogen atom may be replaced by an oxygen atom, or in case NR$^{210}$R$^{220}$ and R$^{110}$ are bonded to adjacent carbon atoms, R$^{110}$ and R$^{210}$ or R$^{110}$ and R$^{220}$—together with the nitrogen atom of the moiety NR$^{210}$R$^{220}$ and the carbon atom to which the moieties NR$^{210}$R$^{220}$ and R$^{110}$ are bonded—form a five- or six-membered ring in which one CH$_2$ group not adjacent to the nitrogen atom may be replaced by an oxygen atom and which five- or six-membered ring may be fused to another five- or six-membered saturated or unsaturated ring, R$^{250}$ and R$^{260}$ are each independently $C_1$-$C_{10}$-alkyl which in case of $C_2$-alkyl may be interrupted by one and in case of $C_3$-$C_{10}$-alkyl by one or two nonadjacent oxygen atoms, $C_5$-$C_7$-cycloalkyl, aryl, aryl-$C_1$-$C_{10}$-alkyl or aryloxy-$C_1$-$C_{10}$-alkyl, Z is O or S, when m=2 the donor moiety D is selected from the group consisting of:

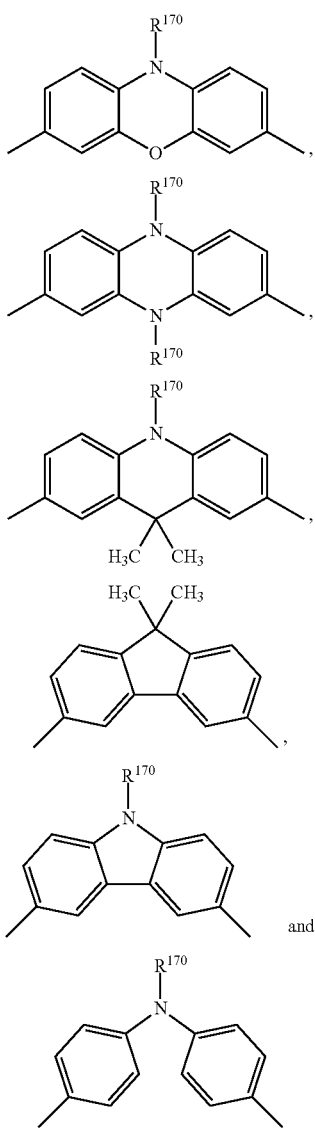
wherein R$^{170}$ is defined above and in case of two moities may vary independently of each other, and
when m=3 the donor moiety D is selected from the group consisting of:
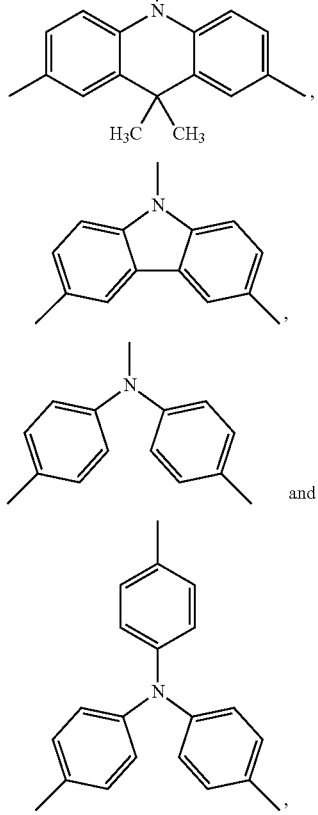
wherein R$^{170}$ is defined above.
4. The compound of claim 1, wherein
when m=1 the donor moiety D is selected from the group consisting of:
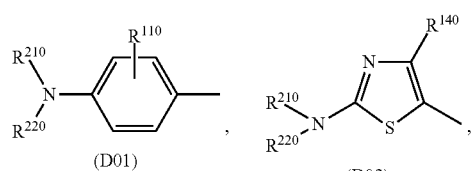
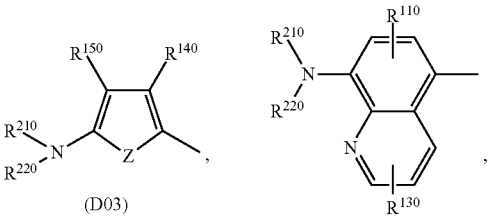
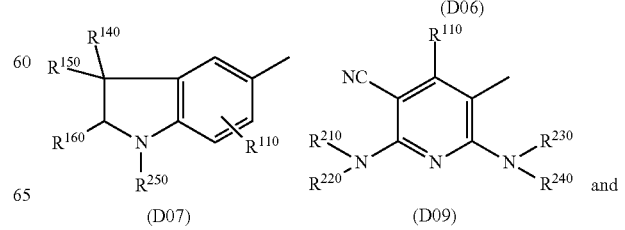

-continued

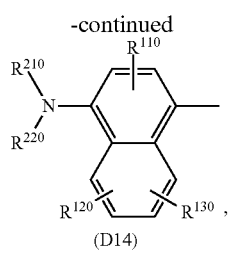
(D14)

when for m=2 the donor moiety D is selected from the group consisting of:

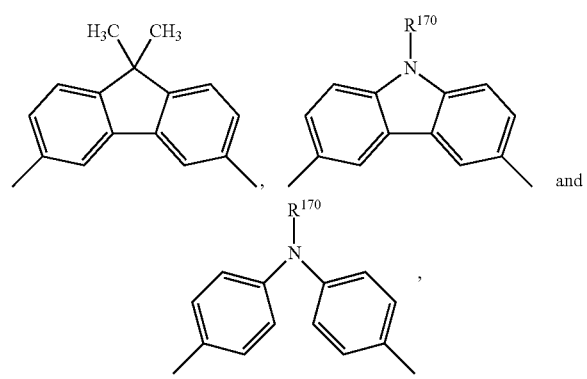

and when m=3 the donor moiety D is selected from the group consisting of:

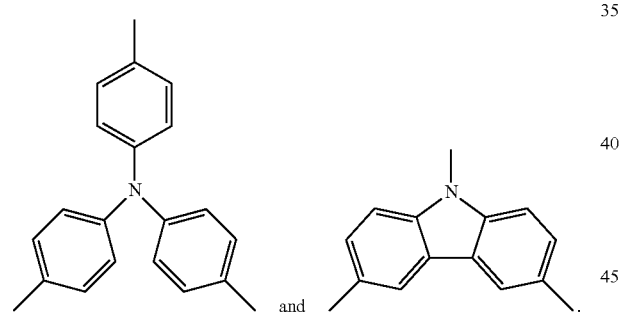

5. The compound of claim 1, wherein
when m=1 the donor moiety D is a represented by formula (D01):

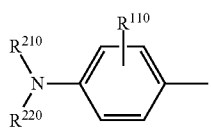
(D01)

$R^{110}$ is hydrogen, halogen, hydroxyl, $C_1$-$C_{10}$-alkyl which in case of $C_2$-alkyl may be interrupted by one and in case of $C_3$-$C_{10}$-alkyl by one or two nonadjacent oxygen atoms, $C_5$-$C_7$-cycloalkyl, $C_1$-$C_{10}$-alkoxy, $C_1$-$C_{10}$-alkylamino, di($C_1$-$C_{10}$-alkyl)amino, $C_1$-$C_{10}$-alkylamino- or di($C_1$-$C_{10}$-alkyl)aminosulfonylamino, $C_1$-$C_{10}$-alkylsulfonylamino, aryl, aryl-$C_1$-$C_{10}$-alkyl, aryloxy-$C_1$-$C_{10}$-alkyl or an —NHCOR$^{170}$ or —NHCOOR$^{170}$ radical, $R^{170}$ is aryl, aryl-$C_1$-$C_{10}$-alkyl, aryloxy-$C_1$-$C_{10}$-alkyl or $C_1$-$C_{10}$-alkyl which in case of $C_2$-alkyl may be interrupted by one and in case of $C_3$-$C_{10}$-alkyl by one or two nonadjacent oxygen atoms, $R^{210}$ and $R^{220}$ are each independently aryl, aryl-$C_1$-$C_{10}$-alkyl, aryloxy-$C_1$-$C_{10}$-alkyl, $C_1$-$C_{10}$-alkyl which in case of $C_2$-alkyl may be interrupted by one and in case of $C_3$-$C_{10}$-alkyl by one or two nonadjacent oxygen atoms, $C_5$-$C_{10}$-cycloalkyl, or $R^{210}$ and $R^{220}$ form, together with the nitrogen atom to which they are bonded, a five- or six-membered ring in which one $CH_2$ group not adjacent to the nitrogen atom may be replaced by an oxygen atom, or in case $NR^{210}R^{220}$ and $R^{110}$ are bonded to adjacent carbon atoms, $R^{110}$ and $R^{210}$ or $R^{110}$ and $R^{220}$—together with the nitrogen atom of the moiety $NR^{210}R^{220}$ and the carbon atom to which the moieties $NR^{210}R^{220}$ and $R^{110}$ are bonded—form a five- or six-membered ring in which one $CH_2$ group not adjacent to the nitrogen atom may be replaced by an oxygen atom and which five- or six-membered ring may be fused to another five- or six-membered saturated or unsaturated ring, when m=2 the donor moiety D is selected from the group consisting of:

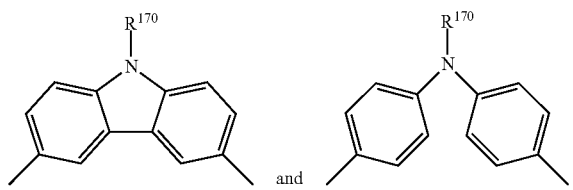

wherein $R^{170}$ is defined above, and when m=3 the donor moiety D is represented by the formula:

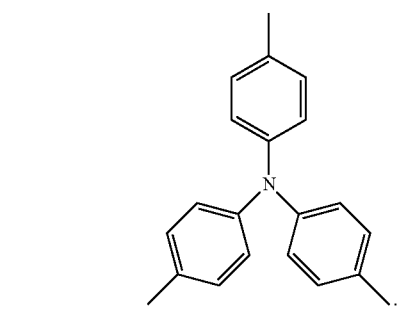

6. The compound of claim 1, wherein the acceptor moiety A is: represented by the formula (A01):

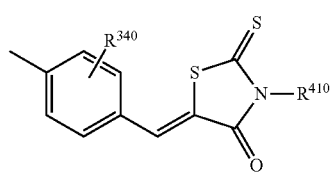
(A01)

wherein
- $R^{340}$ is hydrogen, $NO_2$, CN, $COR^{350}$, $COOR^{350}$, $SO_2R^{350}$ or $SO_3R^{350}$,
- $R^{350}$ is aryl, aryl-$C_1$-$C_{10}$-alkyl, aryloxy-$C_1$-$C_{10}$-alkyl or $C_1$-$C_{10}$-alkyl which in case of $C_2$-alkyl may be interrupted by one and in case of $C_3$-$C_{10}$-alkyl by one or two nonadjacent oxygen atoms,
- $R^{410}$ is hydrogen, $C_1$-$C_{10}$-alkyl which in case of $C_2$-alkyl may be interrupted by one and in case of $C_3$-$C_{10}$-alkyl by one or two nonadjacent oxygen atoms and which may be mono- or polysubstituted by hydroxyl, mercapto, halogen, cyano, nitro, —COOM and/or —COOR$^{420}$, $C_5$-$C_7$-cycloalkyl, aryl, aryl-$C_1$-$C_{10}$-alkyl, aryloxy-$C_1$-$C_{10}$-alkyl, or an —NHCOR$^{420}$ or —N(COR$^{420}$)$_2$ radical where the two $R^{420}$ in the latter may be the same or different,
- M is alkali metal cation or $[NR^{420}]_4^+$, and
- $R^{420}$ is hydrogen, aryl, aryl-$C_1$-$C_{10}$-alkyl, aryloxy-$C_1$-$C_{10}$-alkyl or $C_1$-$C_{10}$-alkyl which in case of $C_2$-alkyl may be interrupted by one and in case of $C_3$-$C_{10}$-alkyl by one or two nonadjacent oxygen atoms.

7. The compound of claim 1, wherein the acceptor moiety A is represented by the formula (A01):

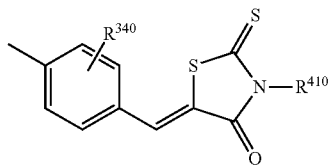

(A01)

wherein
- $R^{340}$ is hydrogen, $NO_2$, CN, $COR^{350}$, $COOR^{350}$, $SO_2R^{350}$ or $SO_3R^{350}$,
- $R^{350}$ is aryl, aryl-$C_1$-$C_{10}$-alkyl, aryloxy-$C_1$-$C_{10}$-alkyl or $C_1$-$C_{10}$-alkyl which in case of $C_2$-alkyl may be interrupted by one and in case of $C_3$-$C_{10}$-alkyl by one or two nonadjacent oxygen atoms,
- $R^{410}$ is aryl or $C_1$-$C_{10}$-alkyl which in case of $C_2$-alkyl may be interrupted by one and in case of $C_3$-$C_{10}$-alkyl by one or two nonadjacent oxygen atoms and which is terminally substituted by hydroxyl, —COOM or —COOR$^{420}$,
- M is alkali metal cation or $[NR^{420}]_4^+$, and
- $R^{420}$ is hydrogen or $C_1$-$C_{10}$-alkyl which in case of $C_2$-alkyl may be interrupted by one and in case of $C_3$-$C_{10}$-alkyl by one or two nonadjacent oxygen atoms.

8. The compound of claim 1, wherein m is 1.

9. The compound of claim 1, wherein m is 2.

10. The compound of claim 1, wherein m is 3.

11. A dye-sensitized solar cell comprising the compound of claim 1.

12. A method of producing a dye-sensitized solar cell comprising incorporating the compound of claim 1 into a dye-sensitized solar cell.

* * * * *